(12) United States Patent
Prais et al.

(10) Patent No.: US 7,632,252 B2
(45) Date of Patent: Dec. 15, 2009

(54) MEDICAL NEEDLE ASSEMBLIES

(75) Inventors: Alfred W. Prais, Hewitt, NJ (US); Richard James Caizza, Vernon, NJ (US); Gary Henniger, Wayne, NJ (US); Espen D. Karteraas, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 46 days.

(21) Appl. No.: 11/744,048

(22) Filed: May 3, 2007

(65) Prior Publication Data

US 2007/0260191 A1  Nov. 8, 2007

Related U.S. Application Data

(63) Continuation of application No. 10/609,146, filed on Jun. 27, 2003, now abandoned, which is a continuation-in-part of application No. 10/141,114, filed on May 9, 2002.

(51) Int. Cl.
  *A61M 5/32* (2006.01)
  *A61M 37/00* (2006.01)
  *A61B 17/20* (2006.01)

(52) U.S. Cl. .......................................... 604/192; 604/46
(58) Field of Classification Search ......... 604/272–274, 604/264, 239, 46, 47, 263, 110, 187, 192, 604/198; 128/919
See application file for complete search history.

(56) References Cited

U.S. PATENT DOCUMENTS

| 3,194,237 | A | * | 7/1965 | Rubin | 604/46 |
| 3,948,261 | A | * | 4/1976 | Steiner | 604/46 |
| 5,868,716 | A | * | 2/1999 | Sweeney et al. | 604/263 |
| 6,298,541 | B1 | * | 10/2001 | Newby et al. | 29/458 |

* cited by examiner

*Primary Examiner*—Matthew F Desanto

(57) ABSTRACT

A shieldable unit dose needle assembly including a needle holding member, a unit dose needle, a shield in pivotal engagement with respect to the needle, and a collar providing pivotal engagement between the needle and the shield. The shield is pivotally movable between a retracted position and a shielded position in which a portion of the shield encompasses the unit dose needle for safety purposes. The needle holding member includes a distal end having a male tapering surface. The collar further includes a proximal end having a female tapering surface in engagement with the male tapering surface of the needle holding member.

17 Claims, 24 Drawing Sheets

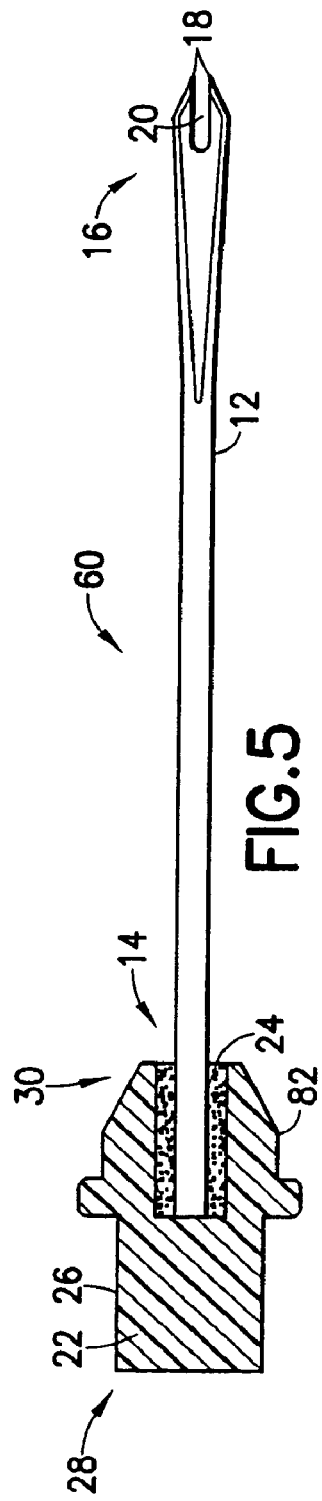
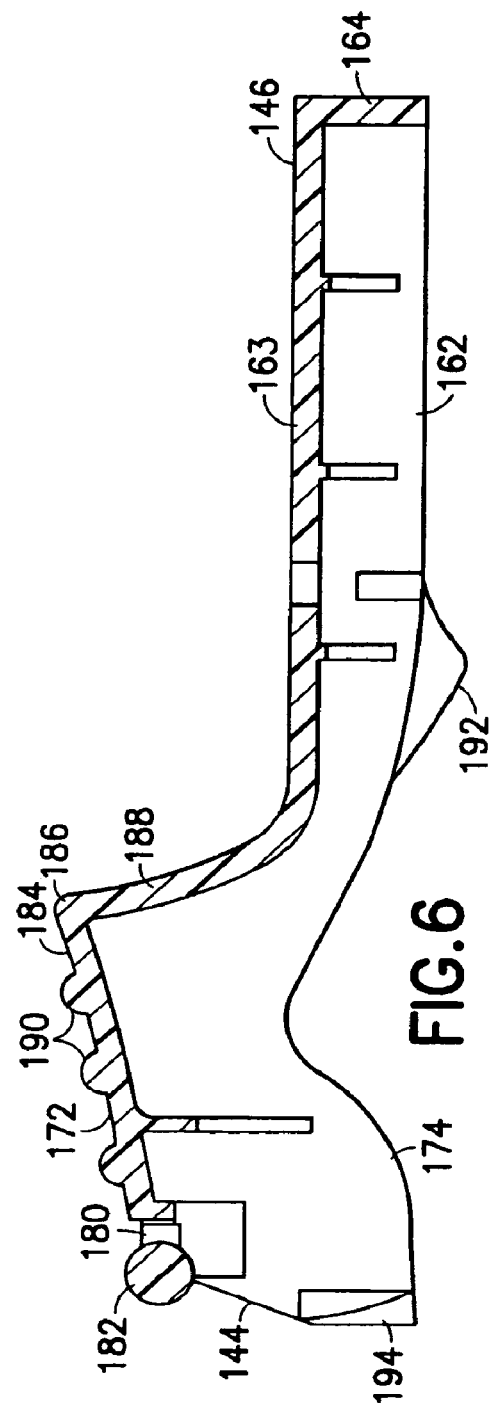

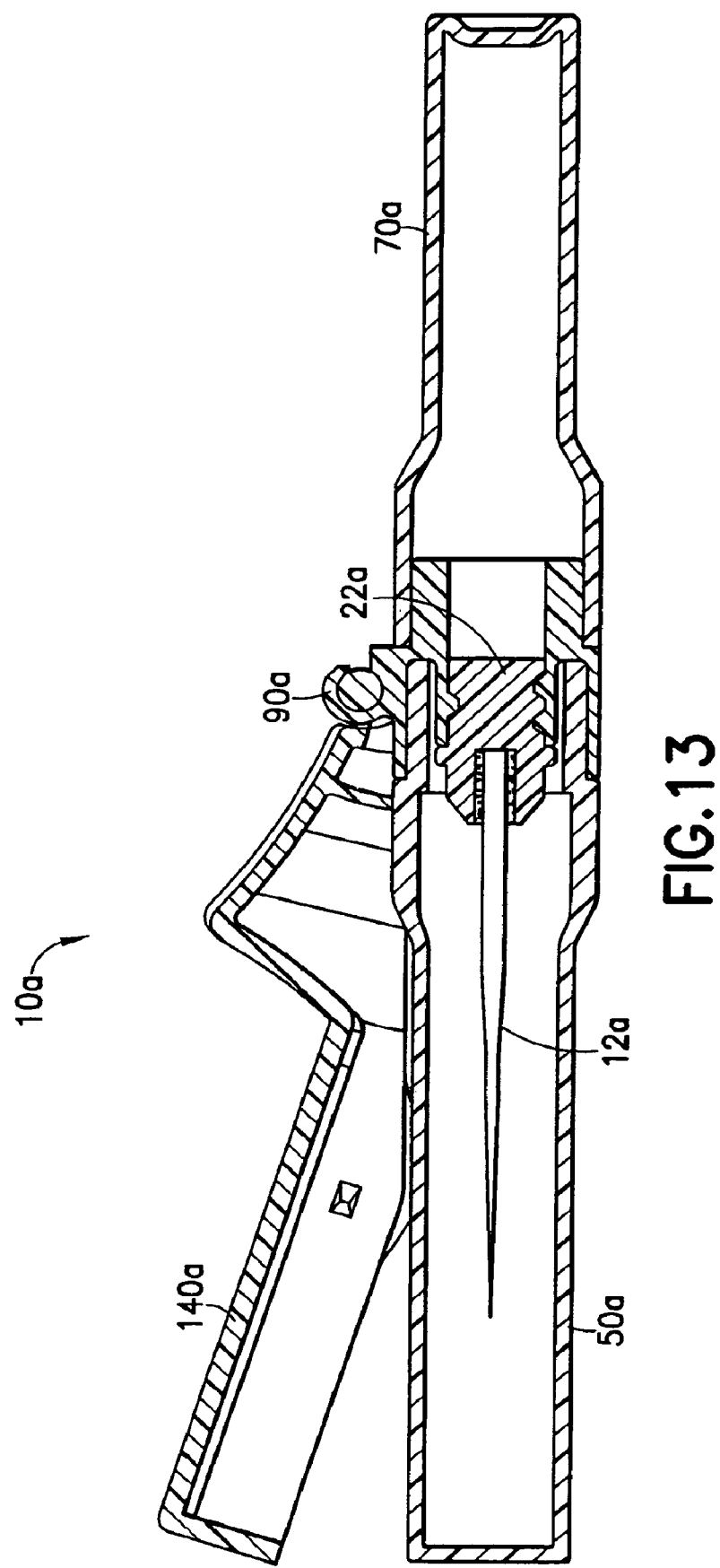

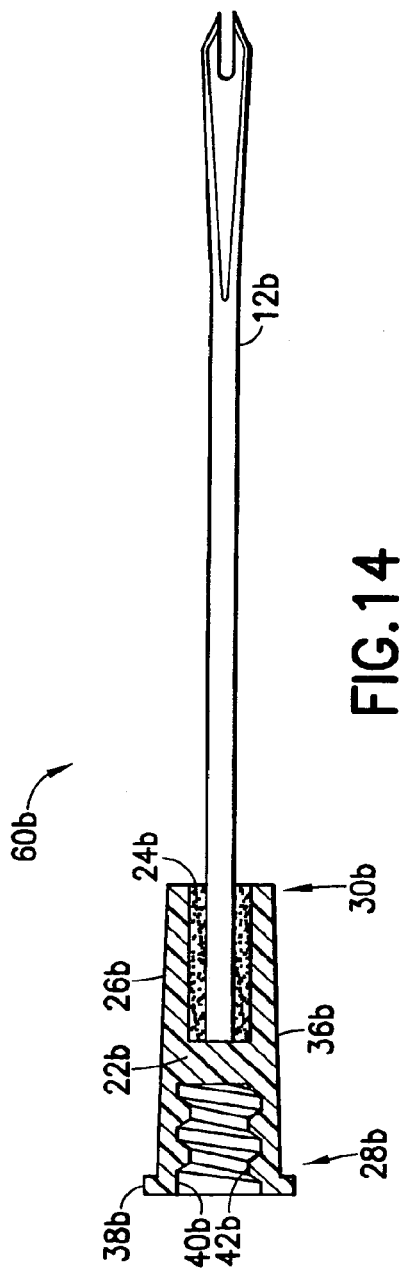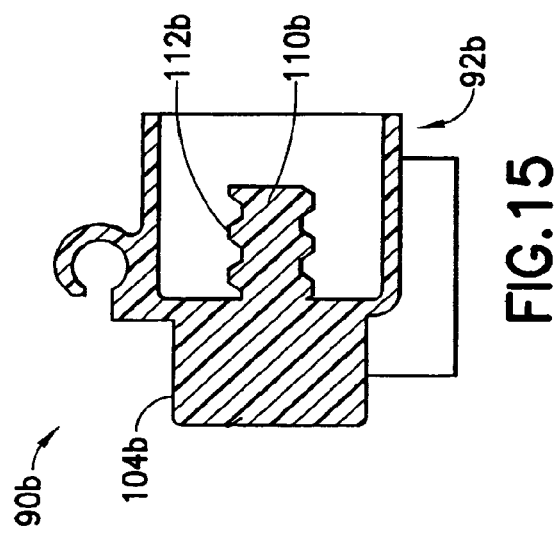

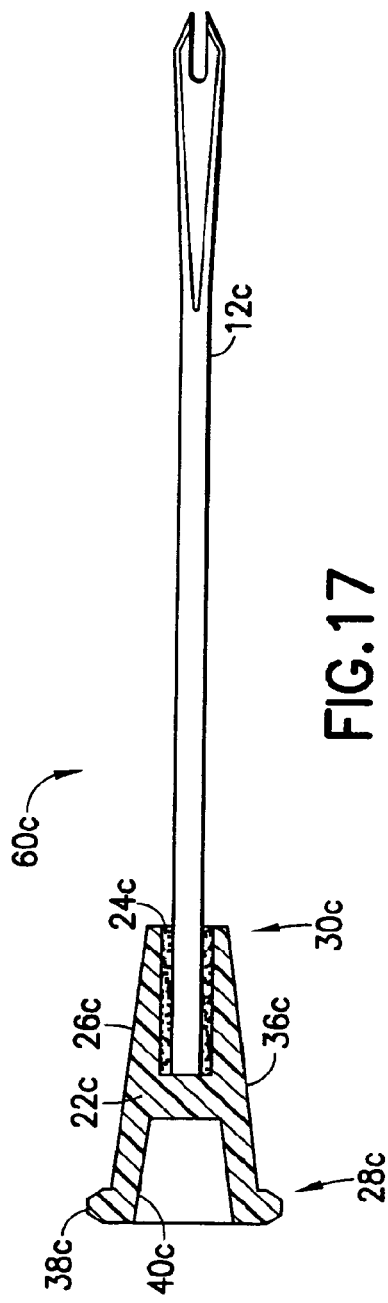
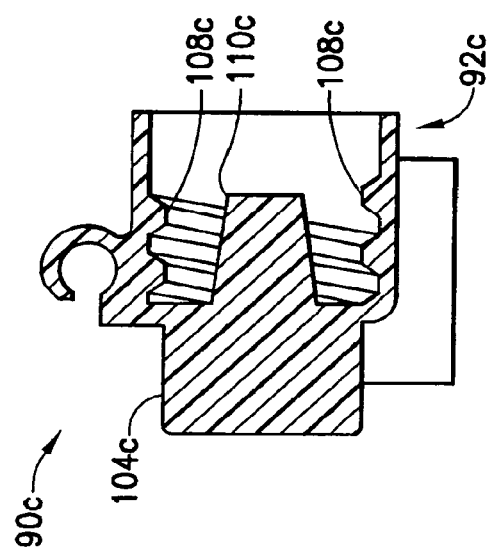

MEDICAL NEEDLE ASSEMBLIES

CROSS-REFERENCE TO RELATED APPLICATIONS

This application is a Continuation of U.S patent application Ser. No. 10/609,146 filed Jun. 27, 2003 now abandoned entitled "Medical Needle Assemblies" which is a Continuation-in-Part of U.S. patent application Ser. No. 10/141,114 filed May 9, 2002 entitled "Medical Needle Assemblies".

BACKGROUND OF THE INVENTION

1. Field of the Invention

The present invention relates to needles for use in medical procedures and, in particular, to safety shielded needles and needle assemblies for use in vaccination procedures.

2. Description of Related Art

Bifurcated or forked end needles are well-known for providing a simple and effective means for a doctor to administer a vaccine. During use, the bifurcated tip of the bifurcated needle is put into contact with either a dried or liquid substance, which adheres to the bifurcated needle tip. The bifurcated needle tip is then put into contact with the skin of the patient who is being administered the vaccination. The skin is either scratched or pierced with the needle tip so that the vaccination material may be absorbed into the skin of the patient. An alternative method of delivering the vaccination includes placing a drop of the vaccine onto the skin of the patient and contacting the skin of the patient with the bifurcated needle tip through the drop of vaccine. Alternatively, a standard pointed needle tip without a lumen may also be used when the drop of vaccine is applied directly to the skin of the patient.

The bifurcated needle is considered a significant medical advancement because it has allowed more people to be vaccinated with less serum. This has been especially important for those living in less developed areas because of the efficient and easy to use design, as well as the ease of replication.

Vaccination effectiveness, however, is reduced if the bifurcated needle is reused too many times. Moreover, reuse of such vaccination needles exposes patients to the risk of transmission of infectious diseases through percutaneous contact through the skin. Additionally, medical care workers using traditional vaccination needles are at an increased risk of exposure to infectious diseases due to the design of such needles, which makes them difficult to handle, as well as due to the repeated use of such needles.

In particular, bifurcated needles used to administer vaccinations are not traditionally sterilized or packaged in a single use container that would enable convenient storage and subsequent use. Additionally, such needles have traditionally been difficult to handle in that they typically do not include a hub attached to the opposite end of a needle from the tip, and do not typically include any sort of shield for protection from the needle prior to and after use.

For example, U.S. Pat. No. 3,194,237 to Rubin discloses a vaccination needle having a main shank with a pair of prongs at one end that define a slot of predetermined length, width and depth therebetween to hold an amount of liquid by capillary action. The shank of the needle is of sufficient length so that the non-prong end will function as a handle. U.S. Pat. No. 3,948,261 to Steiner discloses a reusable unit dose container for vaccines contained within a rigid receptacle, with a compressible closure for supporting a bifurcated needle bearing dried vaccine. The closure is adapted to support the needle in the container during a lyophilizing process while liquid vaccine is dried on the needle. The closure has grooves which permit the vaporized liquid from the vaccine to be withdrawn from the receptacle during lyophilizing, and can further seal the container.

Numerous devices have been developed in the medical field for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies.

For example, U.S. Pat. No. 5,188,611 discloses a reusable safety needle arrangement having a collar for engaging a needle and a slotted longitudinal shield which is attached to the collar at a hinge for pivoting over the needle. Such devices incorporating a pivoting shield assembly are typically used with hypodermic syringe needles or double-ended phlebotomy needles.

While shieldable syringes or needle assemblies are well known in the art for needles used to inject fluids and medicine into the circulatory system of the patient (i.e., venipuncture) such shielding has not previously been used in connection with vaccination needles such as bifurcated needles. In view of the foregoing, a need exists for a shieldable needle assembly for use with a unit dose vaccination needle that is easily manufactured, that is simple to use, that is easily sterilized and maintained in a sterile condition until used, that can be safely disposed of, and that does not interfere with normal practices of bifurcated needle use.

SUMMARY OF THE INVENTION

The present invention is directed to a shieldable unit dose needle assembly for administering a unit dose of a vaccine to a patient. The shieldable assembly includes a needle holding member having a proximal end and a distal end, with the distal end including a male tapering surface. The shieldable assembly also includes a unit dose needle having a handle end and a prong end configured to hold a unit dose of a vaccine. The shieldable assembly further includes a collar having a proximal end and a distal end including a needle end, with the unit dose needle extending from the needle end of the collar. The collar surface includes a proximal end having a female tapering surface in engagement with the male tapering surface at the distal end of the needle holding member. The collar provides for pivotal movement of the shield between a retracted position and a shielded position. The shieldable assembly further includes a shield in pivotal engagement with respect to the unit dose needle, and is pivotally movable between the retracted position pivotally spaced from the prong end of the unit dose needle and the shielded position encompassing or enveloping the prong end of the unit dose needle.

The unit dose needle desirably is in the form of a bifurcated needle, with the prong end including at least two pointed prongs which are capable of penetrating or abrading the skin of a patient, and which are separated by a U-shaped or V-shaped channel capable of holding the unit dose of vaccine. The distal end of the needle holding member includes an annular collar having internal threads adjacent the male tapering surface, and the proximal end of the collar includes a structure for threaded engagement with the internal threads of the annular collar when the female tapering surface is in engagement with the male tapering surface.

The shieldable assembly further includes a projection member coupled to the collar end and a top surface including an outwardly and a distally extending tab. The shield includes a first ramp that is able to contact the projection member when the shield is rotated to the retracted position. The projection member desirably is flexibly mounted to the collar.

The shieldable assembly further includes a means for preventing pivotal movement of the shield between the shielded position and the retracted position after the shield has been pivoted to the shielded position. The shield may be pivotally connected to the collar through a hinged connection established by a hanger bar located on the shield and a hook arm located on the collar, or through a living hinge extending between the shield and the collar.

In a further embodiment, a unit dose needle assembly and a needle holding assembly form a shieldable assembly for administering a unit dose of a vaccine. For example, the unit dose needle assembly includes a collar having a female tapering surface at a proximal end thereof and a solid elongated unit dose needle extending from a distal end thereof. The unit dose needle has a length capable of retrieving a unit dose of a vaccine from a separate container and having a patient end containing and administering the unit dose of a vaccine. The needle holding assembly has an elongated body with a proximal end and a distal end. The distal end includes a male tapering surface in engagement with the female tapering surface of the collar of the unit dose needle assembly. The distal end also includes an annular collar having internal threads in threaded engagement with corresponding structure on the proximal end of the collar. The needle holding assembly further includes a shield in pivotal engagement with respect to the unit dose needle assembly and is pivotally movable between a retracted position pivotally spaced from the patient end of the unit dose needle and a shielded position encompassing the patient end of the unit dose needle.

DESCRIPTION OF THE DRAWINGS

FIG. 5 is a cross-sectional view of the needle hub as shown in FIG. 2 taken along lines 5-5 thereof;

FIG. 6 is a cross-sectional view of the shield as shown in FIG. 2 taken along lines 6-6 thereof;

FIG. 13 is a cross-sectional side view of a shieldable assembly including the unit dose needle assembly of FIG. 11;

FIG. 14 is a cross-sectional view of an alternate unit dose needle assembly for use in a shieldable assembly in accordance with a further embodiment of the present invention;

FIG. 15 is a cross-sectional view of a collar for engagement with the unit dose needle assembly of FIG. 14;

FIG. 17 is a cross-sectional view of a further alternate unit dose needle assembly for use in a shieldable assembly in accordance with a further embodiment of the present invention;

FIG. 18 is a cross-sectional view of a collar for engagement with the unit dose needle assembly of FIG. 17;

DETAILED DESCRIPTION

Figure 1:
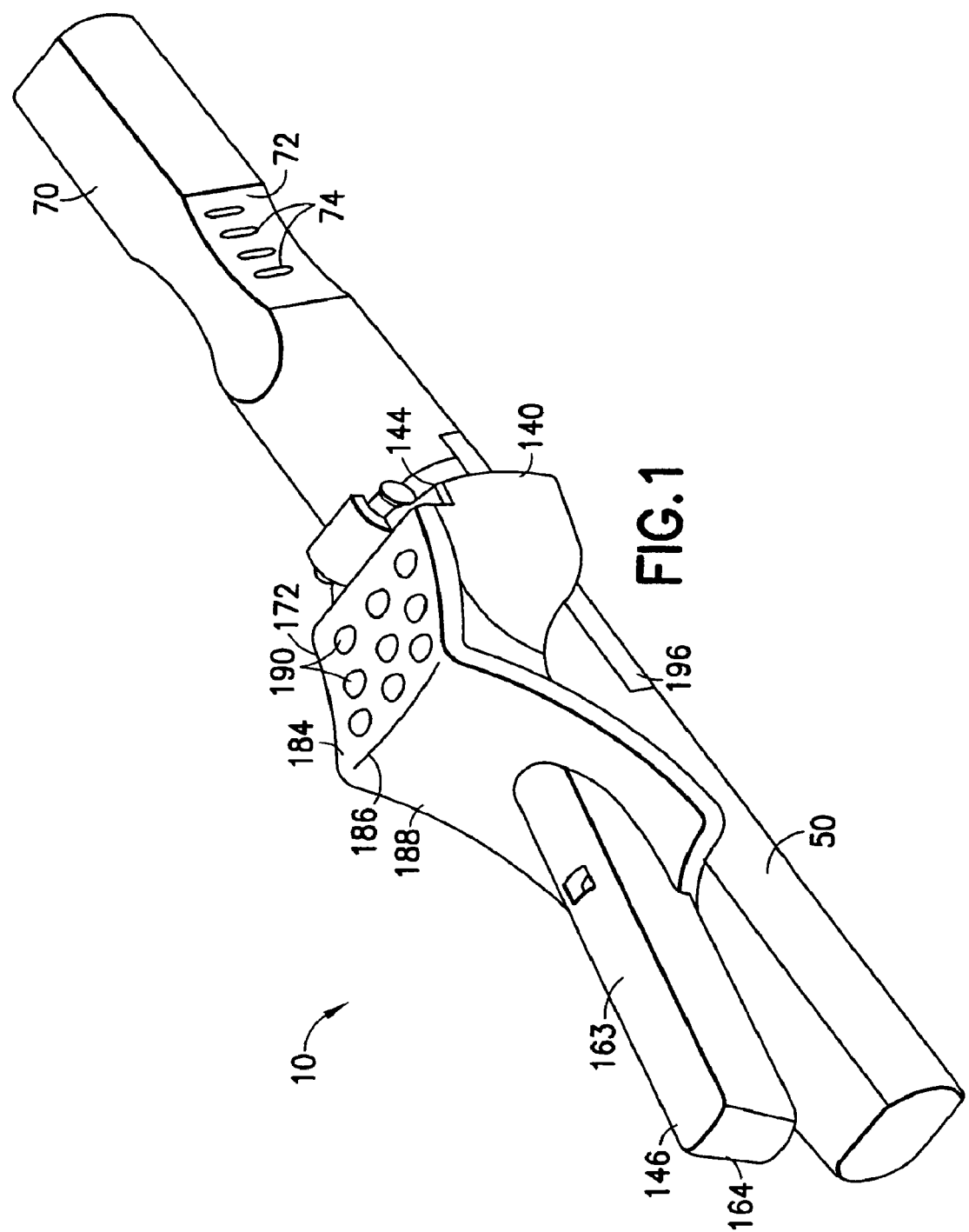
FIG. 1 is a perspective view of the shieldable unit dose needle assembly of the present invention including related packaging features.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
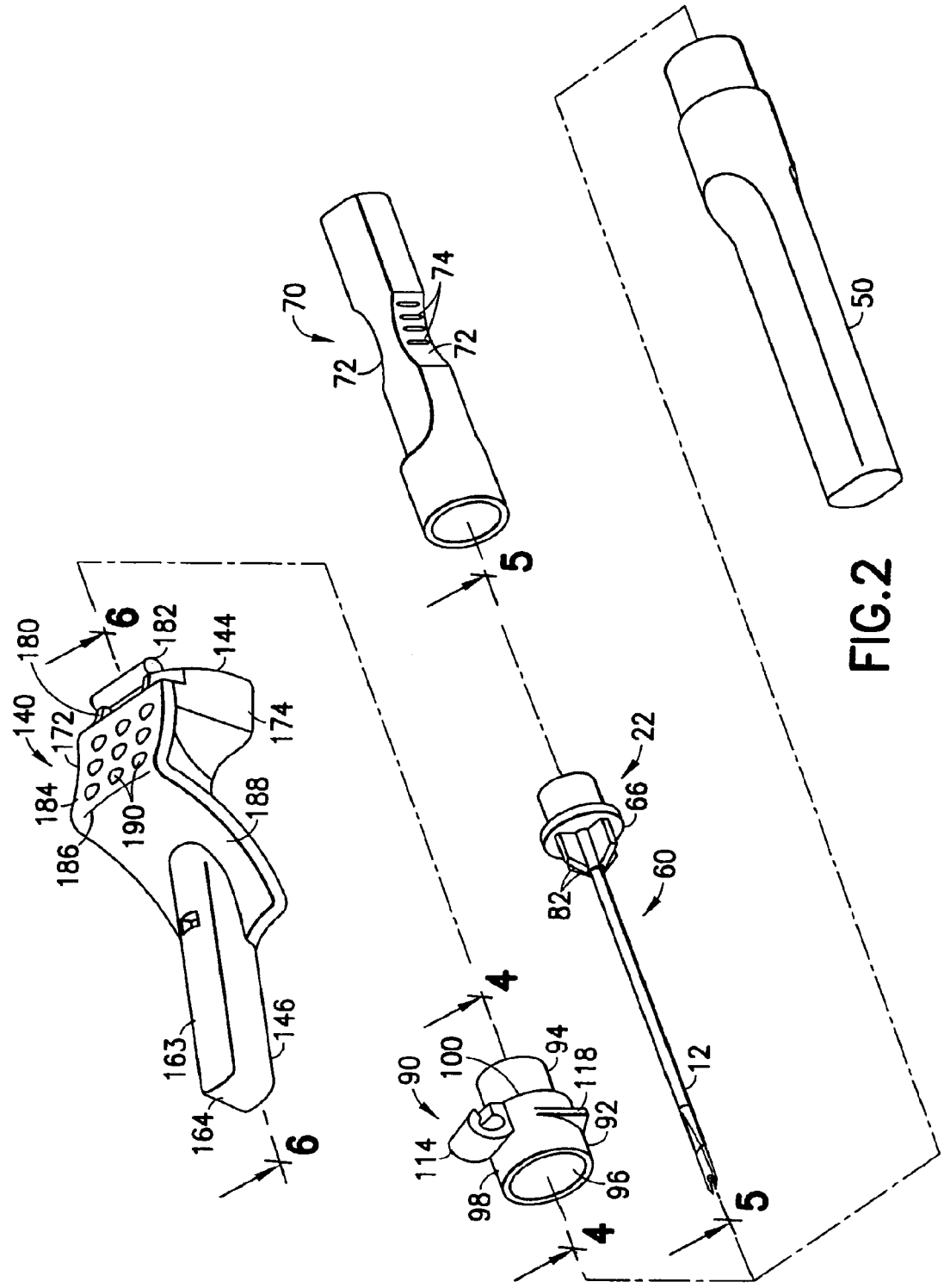
FIG. 2 is a perspective view of the unassembled pieces of FIG. 1.

Referring to the drawings in which like reference characters refer to like parts throughout the several views thereof, FIGS. 1 and 2 illustrate a shieldable unit dose needle assembly 10 in accordance with the present invention, and the related packaging features. The shieldable needle assembly 10 includes a unit dose needle such as a bifurcated needle 12 and a hub 22, which together form a single use, unit dose needle assembly 60. The shieldable needle assembly 10 further includes a safety shield assembly including a collar 90, a housing in the form of a pivotable shield 140, and a handle 70.

The needle assembly 10 of the present invention is intended for use for the administration of vaccines applied to or through the skin of the patient, and is intended as a single use vaccination needle assembly including features to maintain sterility of the needle during packaging, and to provide safety shielding for the medical practitioner after use, as will be described in more detail herein.

The needle assembly 10 includes a unit dose needle assembly 60, as shown in FIGS. 2 and 5. The unit dose needle assembly 60 generally includes a unit dose needle for administering a unit dose of a vaccine, such as a bifurcated needle 12, which is supported by a hub 22. While needle assembly 10 is described herein in terms of a preferred embodiment including a bifurcated needle 12 as the unit dose needle, needle assembly 10 may include any unit dose needle capable of administering a unit dose of a vaccine, such as in a lyophilized dry form or liquid form, as is well-known in the art.

The bifurcated needle 12 includes a handle end at proximal end 14, and an opposed prong end at distal end 16. Bifurcated needle 12 is provided with two sharp prongs 18 positioned at a distal end 16 of the needle. The prongs 18 are separated by a U-shaped channel 20 configured to hold a unit dose of vaccine. The prongs 18 are intended to penetrate or abrade the skin of the patient to administer the vaccine disposed in the U-shaped channel 20. Bifurcated needle 12 may be constructed of any material known in the art, such as metal or plastic, and is desirably constructed of a medical grade surgical steel.

Needle assembly 10 may further include a hub 22 fixedly attached to the proximal end 14 of bifurcated needle 12, such as through an adhesive joint 24. Adhesive joint 24 may be provided through any adhesive capable of fixedly attaching or adhering bifurcated needle 12 to hub 22, such as an oven or U.V. cured epoxy or equivalent adhesive. Hub 22 includes a hub housing 26 including a proximal end 28 and a distal end 30. Desirably, distal end 30 of hub 22 includes an internal bore having an internal diameter of approximately the same size as or a slightly larger size than the outer diameter of the proximal end 14 of bifurcated needle 12, for accommodating and fixedly adhering bifurcated needle 12 within such an internal bore of hub 22.

As noted above, unit dose needle assembly 60 including bifurcated needle 12 and hub 22 are interengaged with a safety shield assembly, thus providing a shieldable feature for bifurcated needle 12 after use. As shown in FIGS. 1 and 2, this shieldable feature is achieved through a shield assembly including collar 90, shield 140, and handle 70. Collar 90 acts as a fitting for mating shield 140 and handle 70 with bifurcated needle 12 through hub 22.

Figure 4:
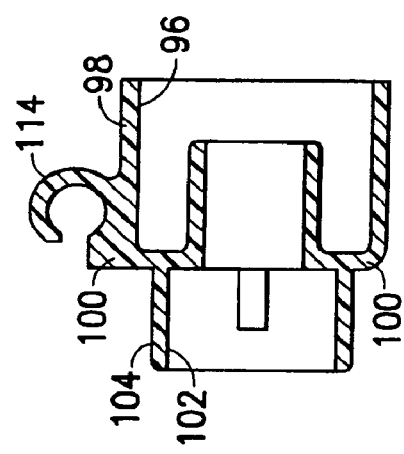
FIG. 4 is a cross-sectional view of the collar as shown in FIG. 2 taken along lines 4-4 thereof.
Figure 7:
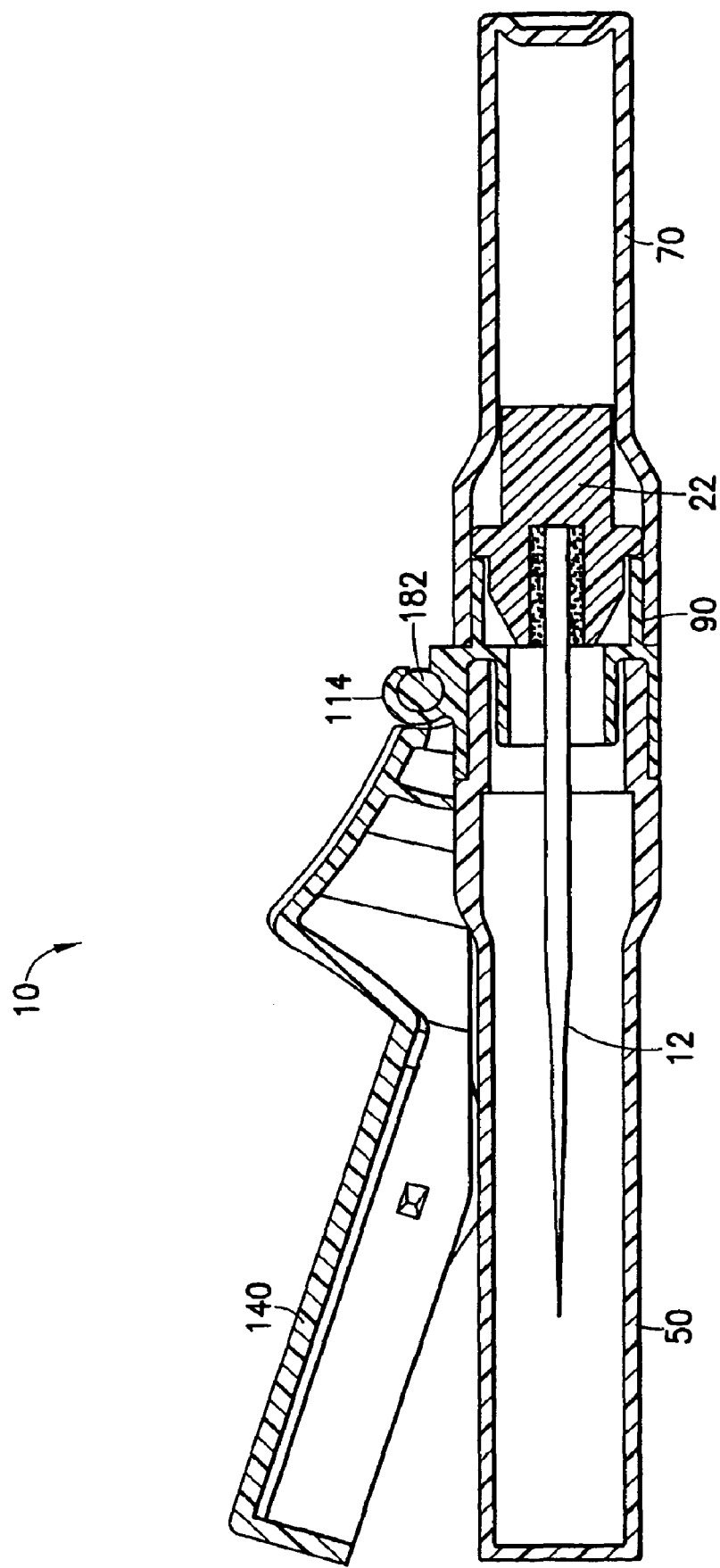
FIG. 7 is a cross-sectional side view of the shieldable assembly of FIG. 1.
Figure 8:
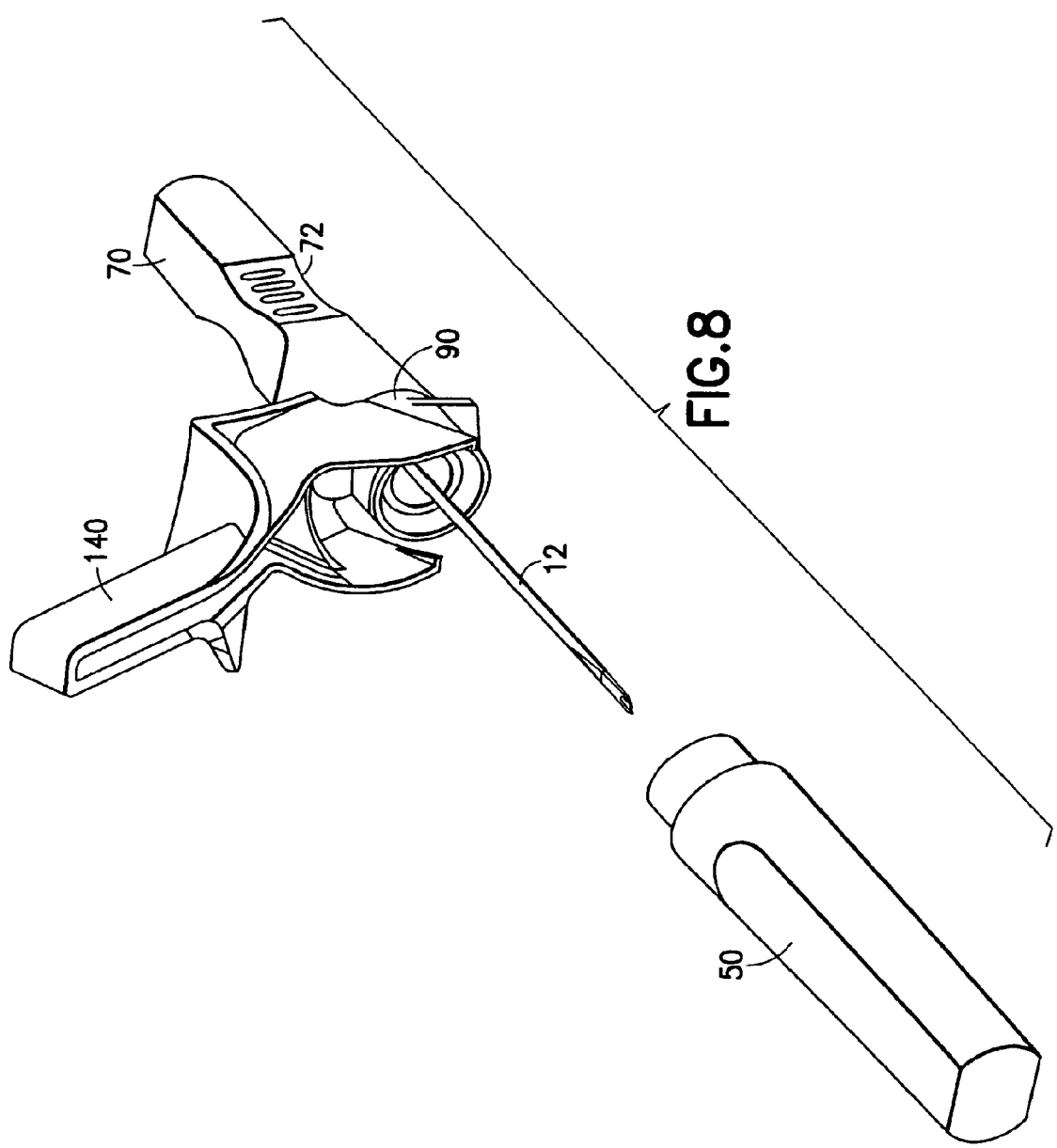
FIG. 8 is a perspective view of the shieldable assembly of FIG. 1 with the needle packaging cover sleeve removed and the shield in a retracted position.

As shown in FIGS. 2 and 4, collar 90 may include two sections, a forward annular skirt 92 at a distal end thereof, and a rearward annular skirt 94 at a proximal end thereof. The forward annular skirt 92 is cylindrical, including an inner sidewall 96 and an outer sidewall 98, and mates with the rearward annular skirt 94 at a shoulder 100. Rearward annular skirt 94 is cylindrical, including an inner sidewall 102 and an outer sidewall 104, and extends from shoulder 100 opposite of forward annular skirt 92. The inner diameter of forward annular skirt 92 is larger than the inner diameter of rearward annular skirt 94. Alternatively, the inner diameters for collar 90 can be formed as a constant inner diameter.

Extending on outer sidewall 98 of forward skirt section 92 is a hook member 114, and located opposite or downwardly of hook member 114 on outer sidewall 98 are latches in the form of locking dents or protrusions 118.

Collar 90 further includes handle 70 extending from the proximal end thereof adjacent rearward annular skirt 94. Handle 70 may be integrally formed with collar 90, or may be a distinct and separate piece as shown in FIG. 2, which is force fitted and affixed onto outer sidewall 104 of rearward annular skirt 94 of collar 90, such as with an adhesive, solvent welding, ultrasonic welding, snap fit, or other equivalent method. Handle 70 may be of a solid construction, or may be hollow with an internal cavity. In such an embodiment, bifurcated needle 12 may extend entirely through hub 22 and into the hollow internal cavity of handle 70, which may facilitate manufacturing and assembling of the needle assembly 10.

Handle 70 provides a medical practitioner with a surface area for grasping and using needle assembly 10 during administration of a vaccine, as will be discussed in more detail herein. Accordingly, handle 70 includes a surface area capable of accommodating a practitioner's fingers for use, and is therefore desirably somewhat elongated in structure. The length of the handle 70 is optimized to provide beneficial ergonomic conditions for administering the vaccination or performing other medical procedures utilizing the bifurcated needle 12. Additionally, handle 70 desirably includes a specific profile for accommodating a user's fingers, such as arcuate surfaces 72 extending along opposing sides of handle 70. In addition or instead of such arcuate surfaces 72, handle 70 may include structure for effectively grasping needle assembly 10, such as ribs 74 extending along opposing sides of handle 70. Desirably, handle 70 includes such ribs 74 along the arcuate surfaces 72, as shown in FIG. 1.

Figure 3:
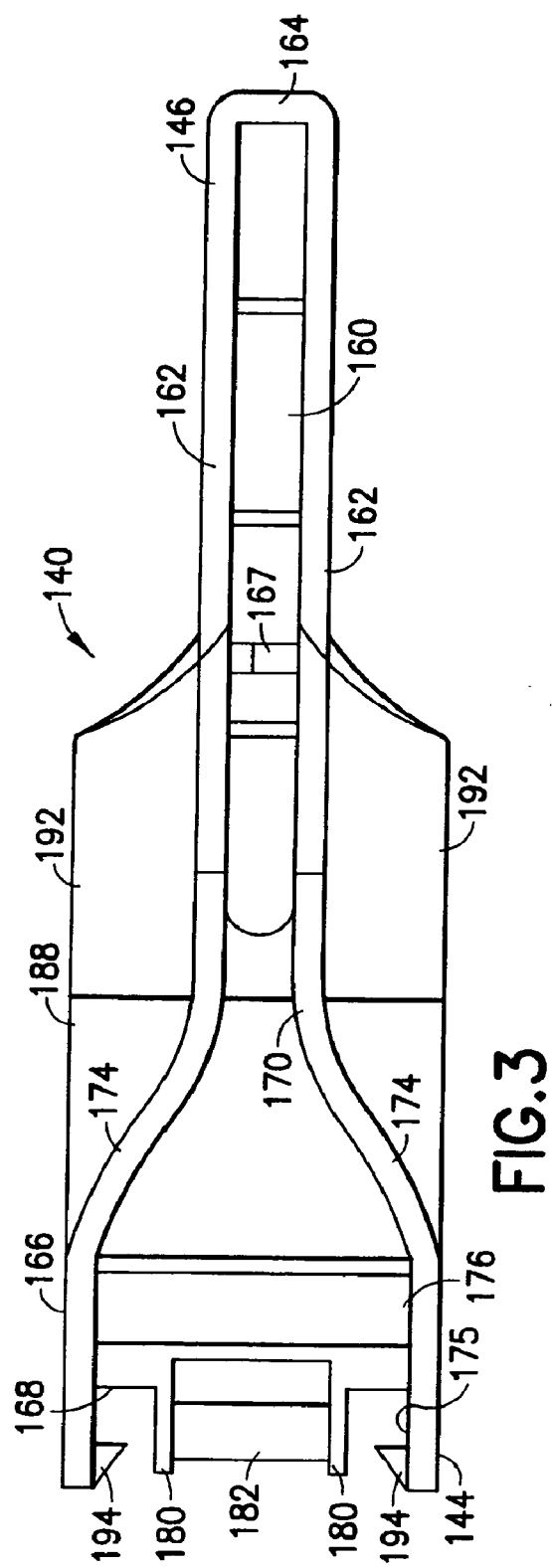
FIG. 3 is a bottom view of the shield as shown in FIG. 2.

As shown in FIGS. 2, 3 and 6, shield 140 comprises a rearward end 144 and a forward end 146. Forward end 146 of shield 140 includes a slot or longitudinal opening 160 formed by sidewalls 162 that extend downwardly from top section 163 and run substantially opposite of one another in parallel along the length of slot 160 toward forward end sidewall 164. Means for trapping and retaining a needle in slot 160 may be provided in the form of an arm 167 that is located at one of sidewalls 162 to secure the used needle.

Arm 167 is deflectable by needle 12 when the needle 12 enters slot 160. Once needle 12 passes the end of arm 167, arm 167 moves back to its original position, whereby needle 12 is permanently trapped in slot 160 by arm 167.

At rearward end 144 of shield 140 is a collar engaging area 166 that is a continuation of slot 160. Collar engaging area 166 includes a rearward end 168, a forward end 170, a top finger guide area 172, parallel sidewalls 174 that extend downwardly and inwardly from top finger guide area 172 and into sidewalls 162, an underside area 176 for surrounding collar 90, and extending arms 180 to hold hanger bar 182. Parallel sidewalls 174 include an inner surface 175 where detents such as barb dents 194 are located.

Top finger guide area 172 comprises a first ramp 184 that extends slightly on an upward slope from the rearward end of collar 90 engaging area to a shoulder 186. From shoulder 186 extends a second ramp 188 which slopes downwardly toward top section 163. Most preferably, first ramp 184 comprises touch bumps 190. Touch bumps 190 provide a tactile and visual guide to alert the user that the user's finger has contacted shield 90 and that the shield is in a defined or controlled position. Touch bumps 190 may be any configuration so long as they extend and are distinct from top finger guide area 172. Touch bumps 190 may also be of a distinguishing color as compared to top finger guide area 172 or shield 140.

Second ramp 188 has interior surface 192 for urging needle 12 toward the center of slot 160 as shield 140 is being rotated into the closed position. The exterior surfaces are slightly inclined and extend radially from second ramp 188. The interior surfaces are especially helpful if the longitudinal axis of needle 12 is misaligned with respect to the longitudinal axis of hub 22.

Figure 9:
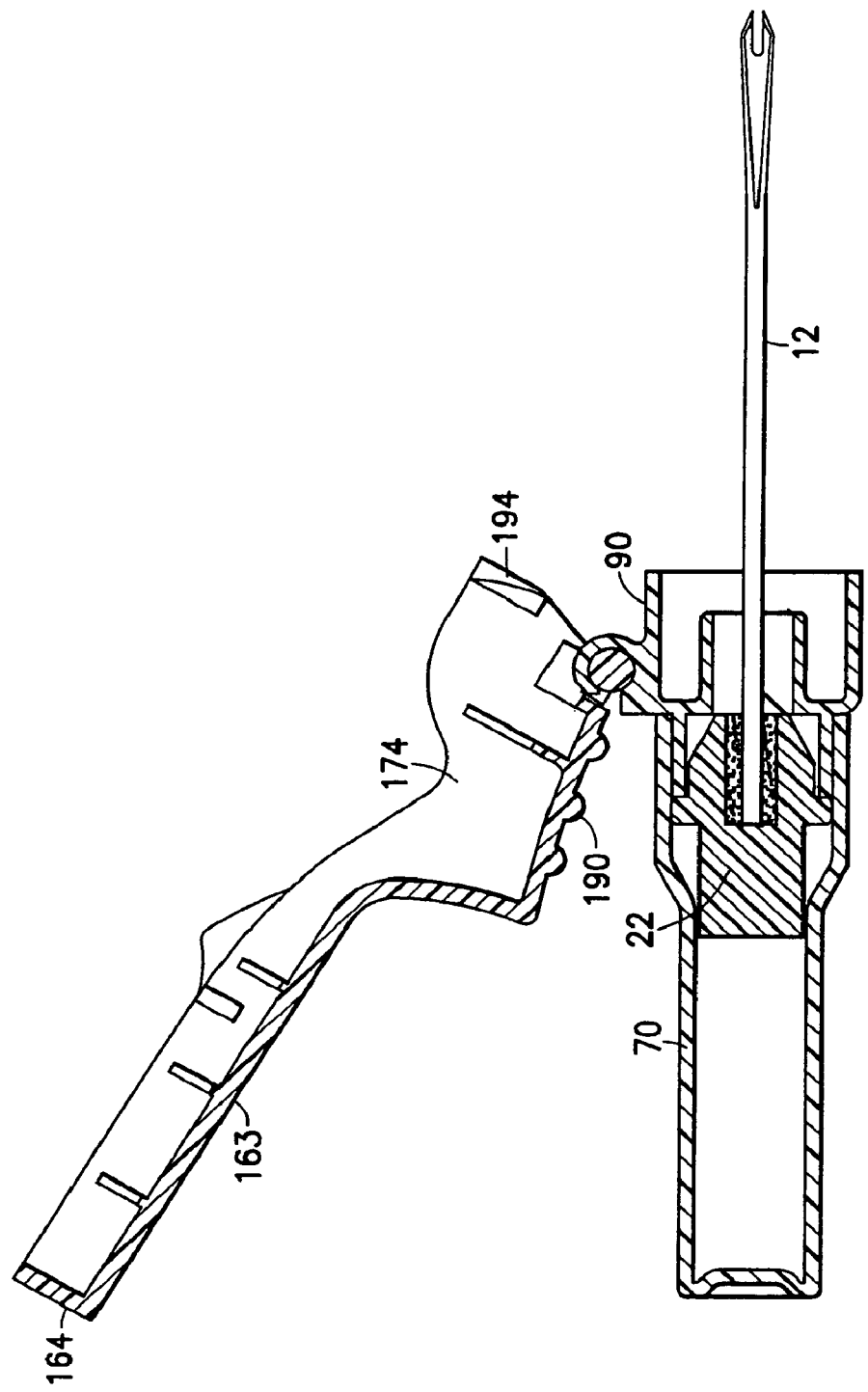
FIG. 9 is a cross-sectional side view of the shieldable assembly of FIG. 1 shown with the needle packaging cover sleeve removed and the shield in a retracted position.
Figure 10:
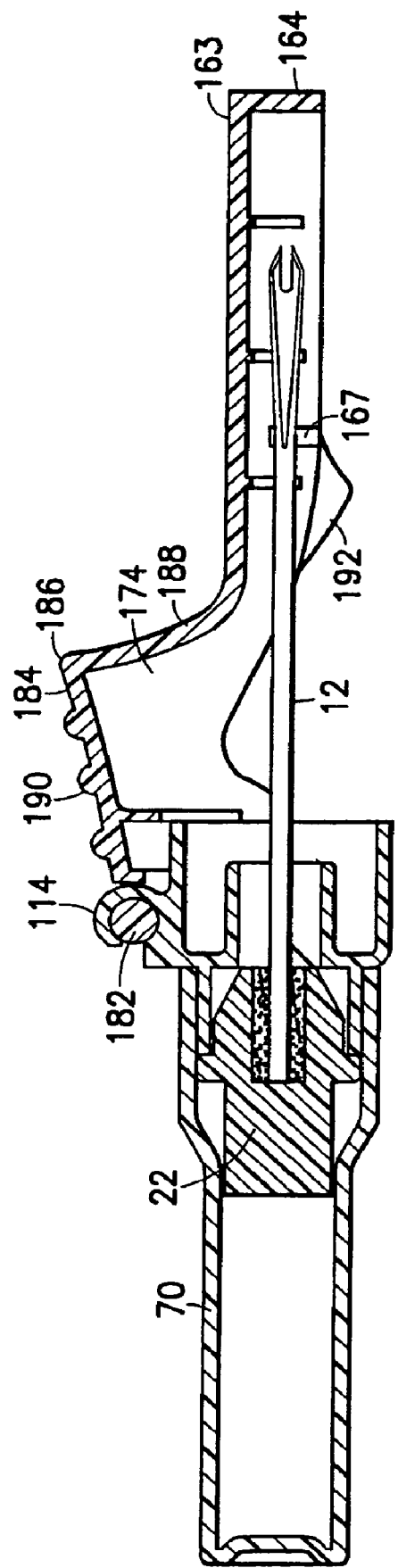
FIG. 10 is a cross-sectional side view of the shieldable assembly of FIG. 1 with the needle packaging cover sleeve removed and the shield in a fully shielded position.

Extending arms 180 are located at rearward end 168 and at the beginning of top finger area 172 and hold hanger bar 182. Hanger bar 182 is provided for pivotal engagement with hook member 114 of collar 90. Accordingly, the cooperating surfaces of hanger bar 182 and hook member 114 are designed so as to permit rotational or pivotal movement of shield 140 with respect to collar 90. Such engagement between hanger bar 182 and hook member 114 provides for pivotal movement of shield 140 between a retracted position as shown in FIG. 9, with shield 140 pivotally spaced from bifurcated needle 12, and a shielded position as shown in FIG. 10, with shield 140 encompassing bifurcated needle 12.

Located downwardly from extending arm 180 and hanger bar 182 and on inner surface 175 of parallel sidewalls 174 are barb dents 194. Barb dents 194 cooperate with locking dents 118 on collar 90 to secure shield 140 in its final locked or shielded position.

The safety shield assembly and the unit dose needle assembly are assembled together, whereby bifurcated needle 12 is connected to hub 22 and sealed with adhesive at adhesive joint 24. Hub 22 is then joined with collar 90 in either a fixed or non-fixed manner. Hub 22 can be fixedly joined with collar 90 by such techniques such as ultra-sonic welding techniques or any other bonding techniques, or mechanical fit, whereby rearward annular skirt 94 of collar 90 may be mated with hub 22. Hub 22 may be contained or force fitted within inner sidewall 102 of rearward annular skirt 94 of collar 90. Collar 90 is aligned with distal end 16 of bifurcated needle 12. Then a packaging needle cover 50 which may be in the form of a semi-rigid sleeve is force fitted into inner sidewall 96 of forward annular skirt 92 of collar 90 to cover bifurcated needle 12. Alternatively, needle cover 50 and collar 90 may include interengaging structure for mating therebetween, such as corresponding threaded surfaces for threaded engagement therebetween or slight interference or friction fits therebetween. Thereafter, shield 140 is connected to collar 90 whereby hanger bar 182 is force fitted into hook member 114 with slot 160 facing needle cover 50. Most preferably, shield 140 is connected to collar 90 by a force fit or interface fit between hanger bar 182 and hook member 114. Therefore, shield 140 is always oriented in a stable position and will not move unless movement of the shield 140 is positively initiated by the user. Shield 140 can then be moved toward needle cover 50 for a low profile packaged product. In addition, a label 196 may be applied to the finally assembled parts. The label 196 may be used to provide tamper evidence, thereby prevent tampering of the parts, so that they are not reused.

During assembly and packaging, the needle assembly may be subjected to a sterilization process, such as e-beam, cobalt, or ethylene oxide sterilization processes, as are well known in the art. Needle cover 50 provides a hermetically sealed barrier enclosing bifurcated needle 12 in a sterile environment therein.

FIGS. 11-31 depict further embodiments of the present invention that include many components which are substantially identical to the components of FIGS. 1-10. Accordingly, similar components performing similar functions will be numbered identically to those components of FIGS. 1-10, except that a suffix "a" will be used to identify those similar components in FIGS. 11-13, a suffix "b" will be used to identify those similar components in FIGS. 14-16, a suffix "c" will be used to identify those similar components in FIGS. 17-19, a suffix "d" will be used to identify those similar components in FIGS. 20-21, a suffix "e" will be used to identify those similar components in FIG. 22, and a suffix "f" will be used to identify those similar components in FIGS. 23-31.

Figure 11:
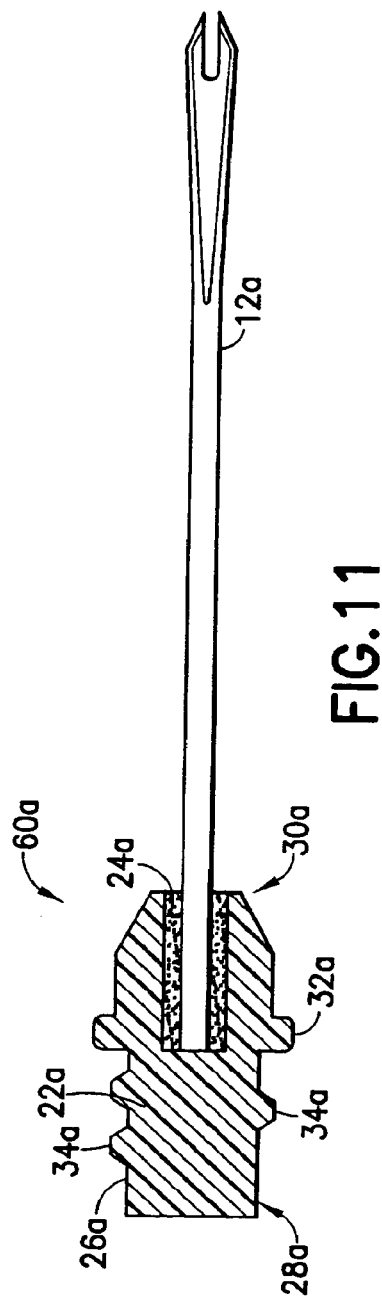
FIG. 11 is a cross-sectional view of a unit dose needle assembly for use with a shieldable assembly in accordance with an alternate embodiment of the present invention.

FIG. 11 depicts an alternate embodiment of a unit dose needle assembly 60*a* for use with a shieldable needle assembly in accordance with the present invention. In the embodiment of FIG. 11, hub 22*a* includes a hub housing 26*a* including a proximal end 28*a* and a distal end 30*a* separated by flange 32*a*. Bifurcated needle 12*a* extends from distal end 30*a* of hub 22*a*, and is affixed thereto through adhesive joint 24*a*. Proximal end 28*a* of hub 22*a* further includes external threads 34*a* for providing interengagement with collar 90*a*.

Figure 12:
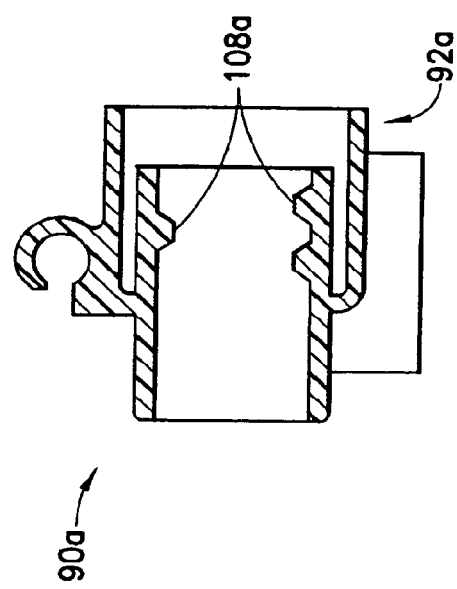
FIG. 12 is a cross-sectional view of a collar for engagement with the unit dose needle assembly of FIG. 11.

More particularly, as shown in FIGS. 12 and 13, collar 90*a* desirably includes internal threads 108*a* extending within forward annular skirt 92*a*. Internal threads 108*a* of collar 90*a* and external threads 34*a* of hub 22*a* provide interengaging threaded structure between collar 90*a* and unit dose needle assembly 60*a*, thereby providing a means for attaching unit dose needle assembly 60*a* to collar 90*a* to provide a shielding feature. As such, unit dose needle assembly 60*a* can be provided as a separate structure which can be attached to a separate shielding structure in the form of a shield assembly including collar 90*a*, shield 140*a* and handle 70*a* by threading external threads 34*a* with internal threads 108*a* of collar 90*a*, thereby providing a shieldable needle assembly 10*a* as shown for use in FIG. 13.

FIG. 14 depicts a further embodiment of a unit dose needle assembly 60*b* for use with a shieldable needle assembly 10*b* in accordance with the present invention. In the embodiment of FIG. 14, hub 22*b* includes a hub housing 26*b* including a proximal end 28*b* and a distal end 30*b*, with bifurcated needle 12*b* extending from and affixed to distal end 30*b* through adhesive joint 24*b*. The external surface of hub housing 26*b* may define an outer tapered surface 36*b* extending thereal ong. Proximal end 28*b* of hub 22*b* further includes a full or partial hub rim 38*b* extending fully or partially circumferentially about the proximal end thereof, with an internal luer taper 40*b* extending internally within a portion of hub housing 26*b*. Internal luer taper 40*b* may further include internal threads 42*b* for providing threaded interengagement with collar 90*b*.

Figure 16:
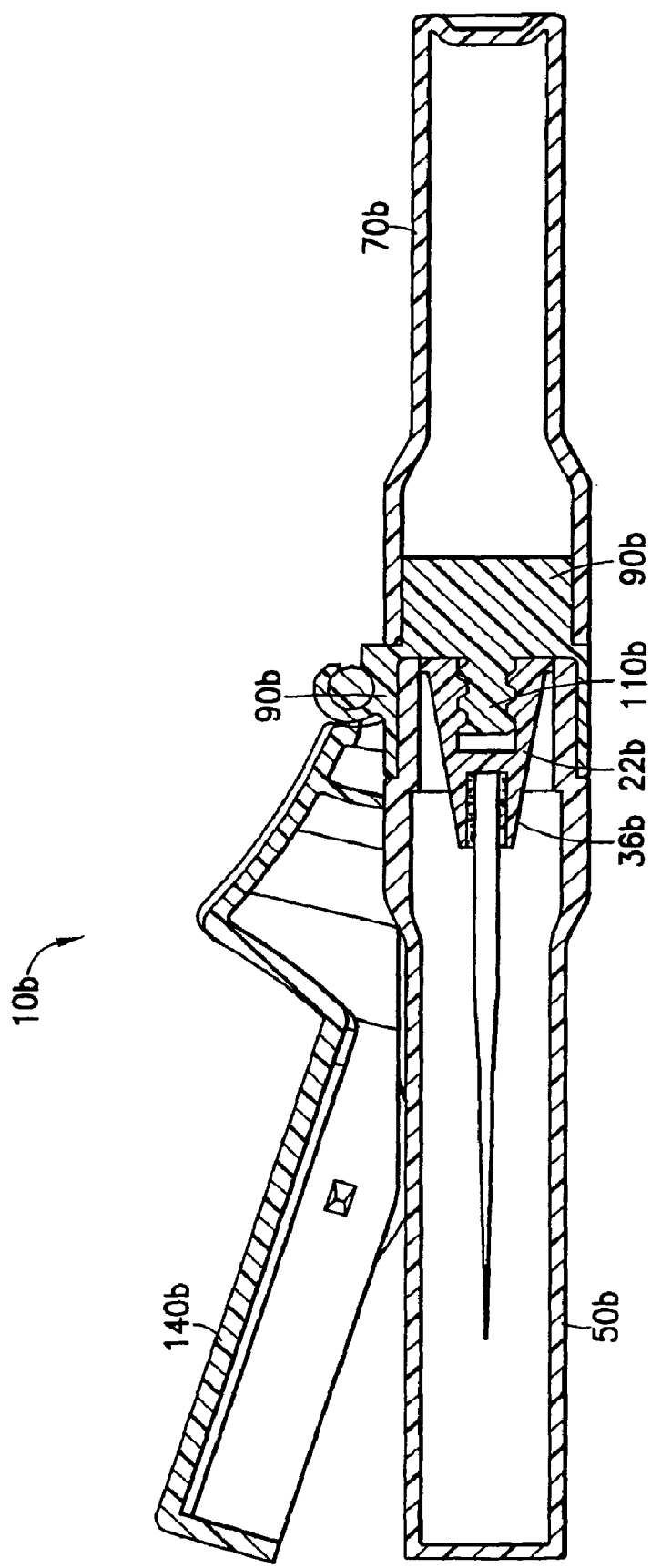
FIG. 16 is a cross-sectional side view of a shieldable assembly including the unit dose needle assembly of FIG. 14.

As shown in FIGS. 15 and 16, collar 90*b* includes a nub 110*b* having external threads 112*b* extending thereabout for threaded engagement with internal threads 42*b* of hub 22*b*, providing interengaging threaded structure therebetween in a similar manner as with the assembly described in FIGS. 11-13. Handle 70*b* is affixed to outer sidewall 104*b*, thereby providing a separate shielding structure in the form of a shield assembly including collar 90*b*, shield 140*b* and handle 70*b* for attachment with unit dose needle assembly 60*b*. In such an arrangement, needle cover 50*b* desirably mates with outer tapered surface 36*b* of hub 22*b*, within forward annular skirt 92*b* of collar 90*b*.

Figure 19:
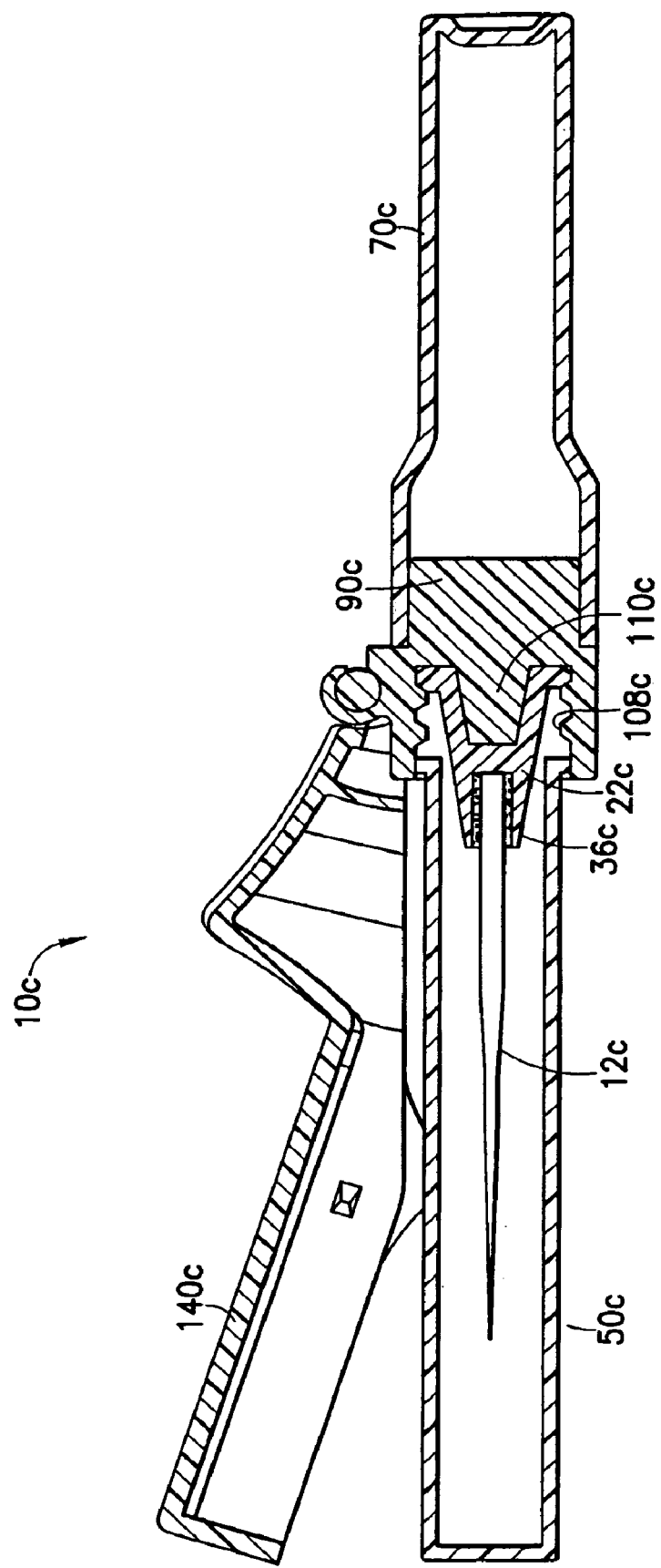
FIG. 19 is a cross-sectional side view of a shieldable assembly including the unit dose needle assembly of FIG. 17.

FIGS. 17-19 depict yet a further embodiment of a unit dose needle assembly 60*c* for use with a shieldable needle assembly 10*c* in accordance with the present invention. In this embodiment, hub 22*c* includes a hub housing 26*c* including a proximal end 28*c* and a distal end 30*c*, with bifurcated needle 12*c* extending from and affixed to distal end 30*c* through adhesive joint 24*c*. The external surface of hub housing 26*c* defines an outer tapered surface 36*c* extending therealong. Proximal end 28*c* of hub 22*c* further includes luer lugs or a hub rim 38*c* extending fully or partially circumferentially about the proximal end thereof, with an internal luer taper 40*c* extending internally within a portion of hub housing 26*c*.

As shown in FIGS. 18 and 19, collar 90c includes a tapered nub 110c, having a profile for mating with the internal surface of internal luer taper 40c of hub 22c. In addition, collar 90c preferably includes internal threads 108c extending within forward annular skirt 92c. Internal threads 108c of collar 90c mate with hub rim 38c of hub 22c, thereby providing interengaging threaded structure between collar 90c and unit dose needle assembly 60c, for attaching unit dose needle assembly 60c to collar 90c to provide a shielding feature. Handle 70c is affixed to outer sidewall 104c. In such a structure, needle cover 50c desirably mates with outer tapered surface 36c of hub 22c, within forward annular skirt 92c of collar 90c. Alternatively, needle cover 50c may include an annular rim extending circumferentially about the end thereof, for threaded engagement with internal threads 108c of collar 90c after hub 22c has been mated therewith.

Figure 20:
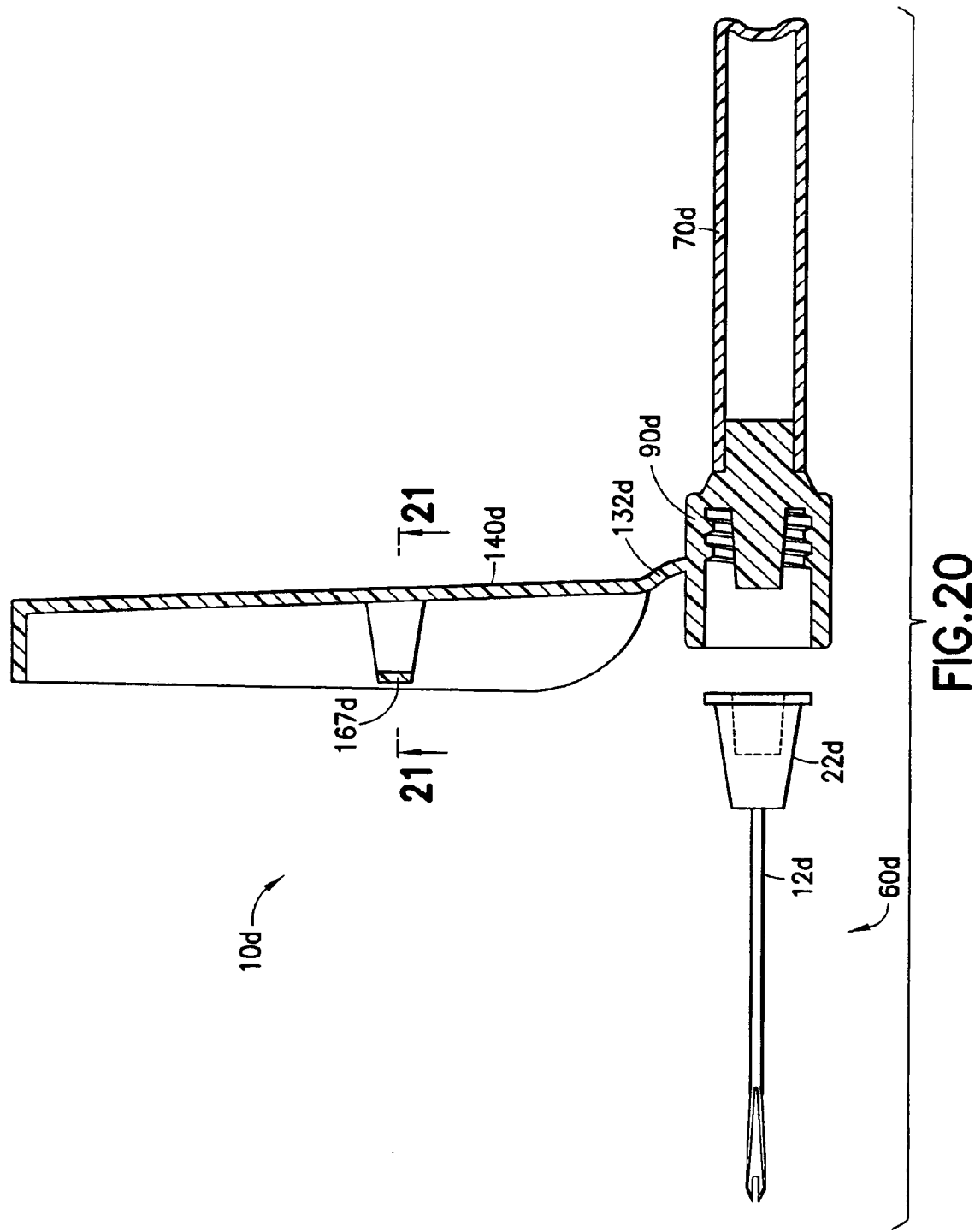
FIG. 20 is a side-sectional view of a shieldable assembly in a further embodiment of the present invention, showing the unit dose needle separated from the shield assembly.
Figure 21:
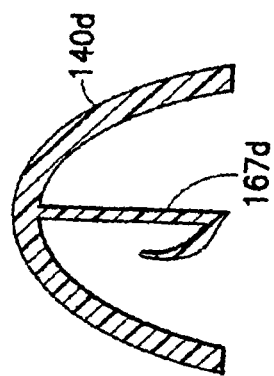
FIG. 21 is a cross-sectional view taken along line 21-21 of FIG. 20.

FIGS. 20 and 21 depict a unit dose needle assembly 60d in combination with a shield assembly including a living hinge 132d extending between collar 90d and shield 140d. Living hinge 132d permits shield 140d to pivot between the retracted position and the shielded position, as discussed with respect to the above embodiments. Living hinge 132d, collar 90d, shield 140d, and handle 70d can be integrally molded and formed as a single shielding structure to form a shield assembly. Unit dose needle assembly 60d can then be attached to such a shield assembly, thereby forming needle assembly 10d. Shield 140d may further include arm 167d, which acts as a locking mechanism with bifurcated needle 12d in a similar manner as described above. Additionally, in an embodiment where living hinge 132d, collar 90d, shield 140d, and handle 70d are integrally molded, bifurcated needle 12d can be assembled through bonding means to a bore (not shown) in the collar to provide an easier to manufacture assembly. Additionally, it is contemplated that bifurcated needle 12d can be integrally molded as an extension from the collar when made from similar moldable materials.

Figure 22:
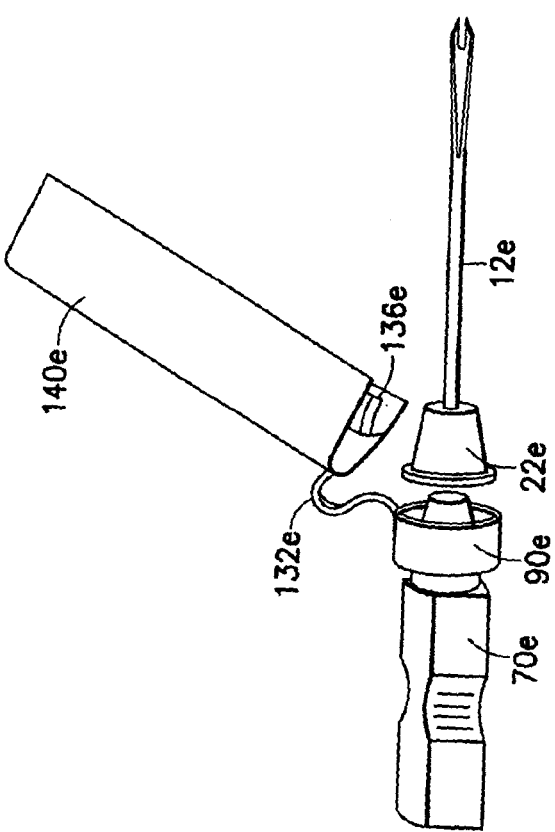
FIG. 22 is a side view of a shieldable assembly in yet a further embodiment of the present invention, showing the rigid packaging cover separated from the needle.
Figure 23:
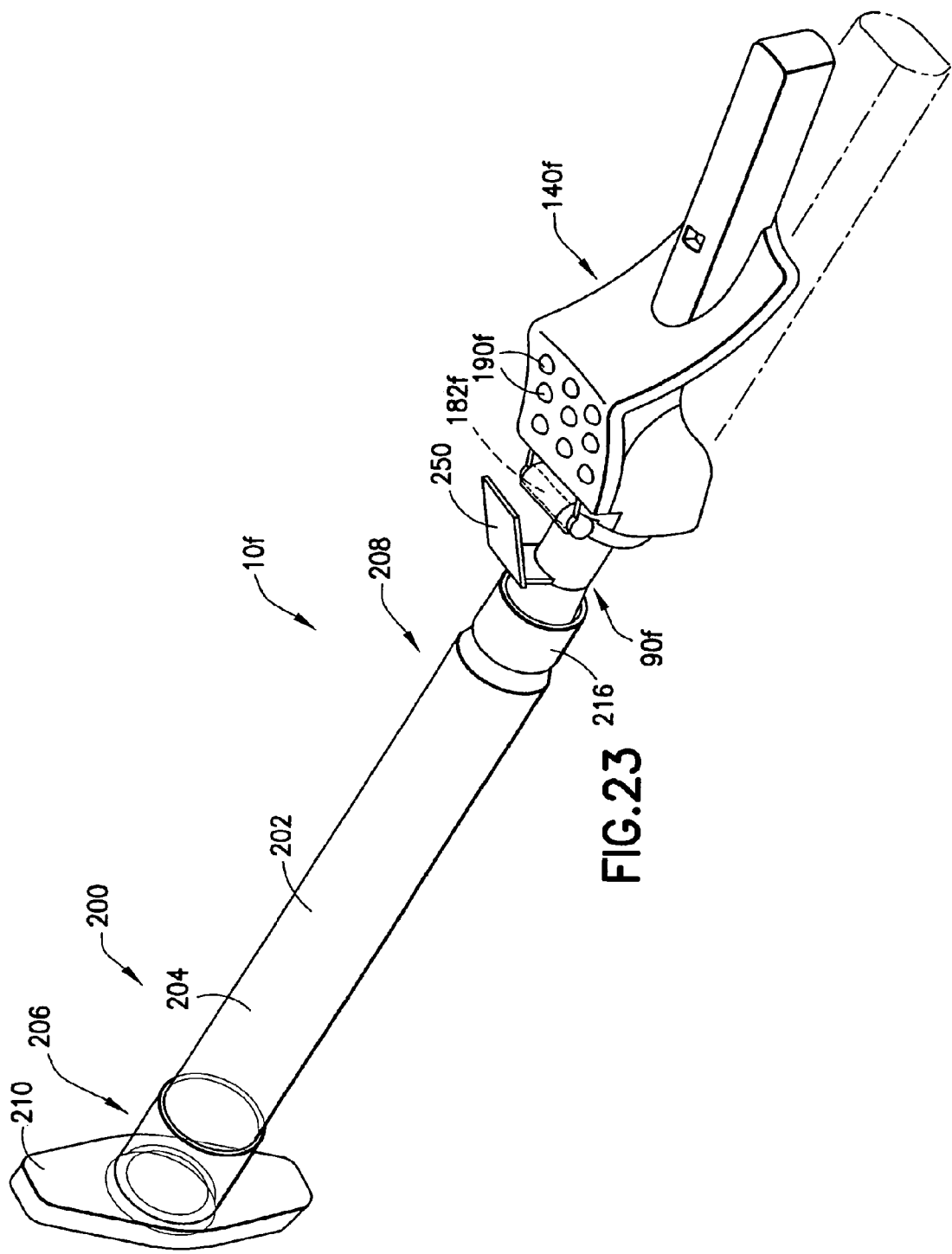
FIG. 23 is a perspective view of a shieldable needle assembly in an alternate embodiment of the present invention with a unit dose needle assembly and a needle holding assembly.

In FIG. 22, a unit dose needle assembly 60e is shown in combination with a shield assembly including a living hinge 132e, with a locking mechanism in the form of an elongated door 136e on shield 140e. Elongated door 136e acts as a locking mechanism with bifurcated needle 12e in a similar manner as described above with respect to arm 167 acting as a means for trapping bifurcated needle 12. Desirably, elongated door 136e extends over substantially the entire length of the longitudinal slot of shield 140e. Elongated door 136e is biased to close the longitudinal slot after shield 140e has been pivoted about living hinge 132e and bifurcated needle 12e is encompassed in shield 140e. Desirably, elongated door 136e is in the form of a trap door extending from a first sidewall of shield 140e to a second sidewall of shield 140e, with the trap door abutting a stop on the second sidewall. A pair of elongated doors may be alternatively provided, each extending from a sidewall of the housing of shield 140e, and with the doors overlapping to close the housing. Desirably, the elongate door member is attached to the shield 140e by a resilient living hinge.

FIGS. 24-31 depict an alternate embodiment of a shieldable needle assembly 10f in accordance with the present invention. The shieldable needle assembly 10f includes a unit dose needle assembly 60f connected to a needle holding assembly 200.

Generally, needle holding assembly 200 includes needle holding member 202 which is defined by a generally cylindrical body 204 extending between proximal end 206 and distal end 208. The cylindrical body 204 may be a hollow member, such as a conventional syringe barrel, or may be a solid member. Proximal end 206 of the body 204 of needle holding member 202 desirably includes structure for grasping needle holding member 202, such as a circumferential flange or a pair of flange tabs 210. The overall dimensions of needle holding member 202 such as the length and circumference are configured so as to provide an appropriate handle portion for effectively grasping the shieldable needle assembly 10f. Desirably, needle holding assembly is a standard 3 cc syringe as is known in the art, but without any internal plunger mechanism as would be conventionally used with a syringe for delivering fluids.

The needle holding member 202 includes a tapered tip 212 projecting distally therefrom at distal end 208. Tapered tip 212 includes a male tapering surface such as a male luer taper 214. It is noted, however, that tapered tip 212 need not have any opening therethrough, and may be a solid member, which may provide additional structural integrity to the tapered tip 212. Needle holding member 202 may also include a luer collar 216 at distal end 208, which is generally adjacent tapered tip 212 and generally surrounds tapered tip 212. Luer collar 216 may include a plurality of internal threads 218 for threadably receiving a hub of the unit dose needle assembly 60f, as explained further herein.

Figure 24:
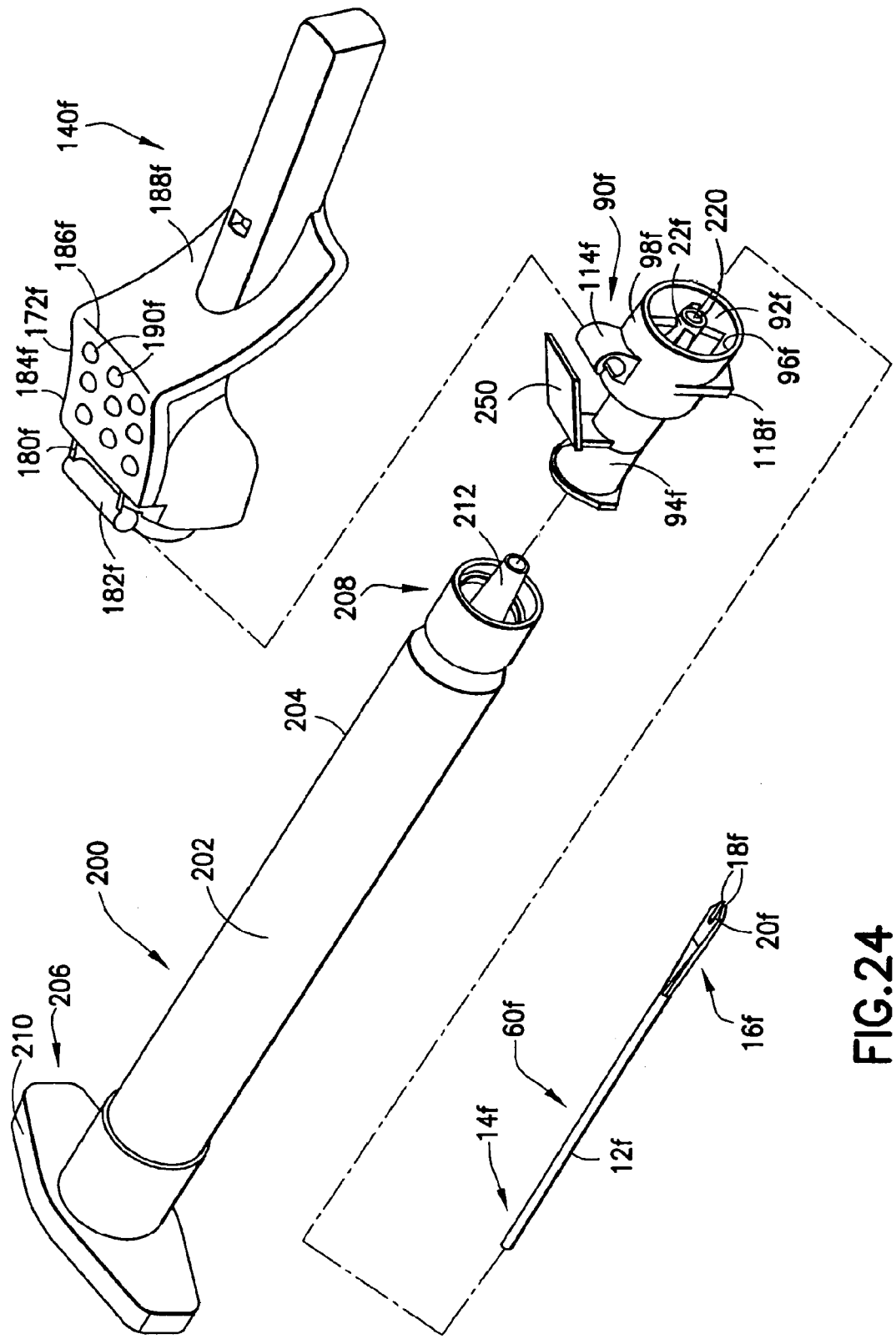
FIG. 24 is an exploded view of the unassembled pieces shown in FIG. 23.
Figure 25:
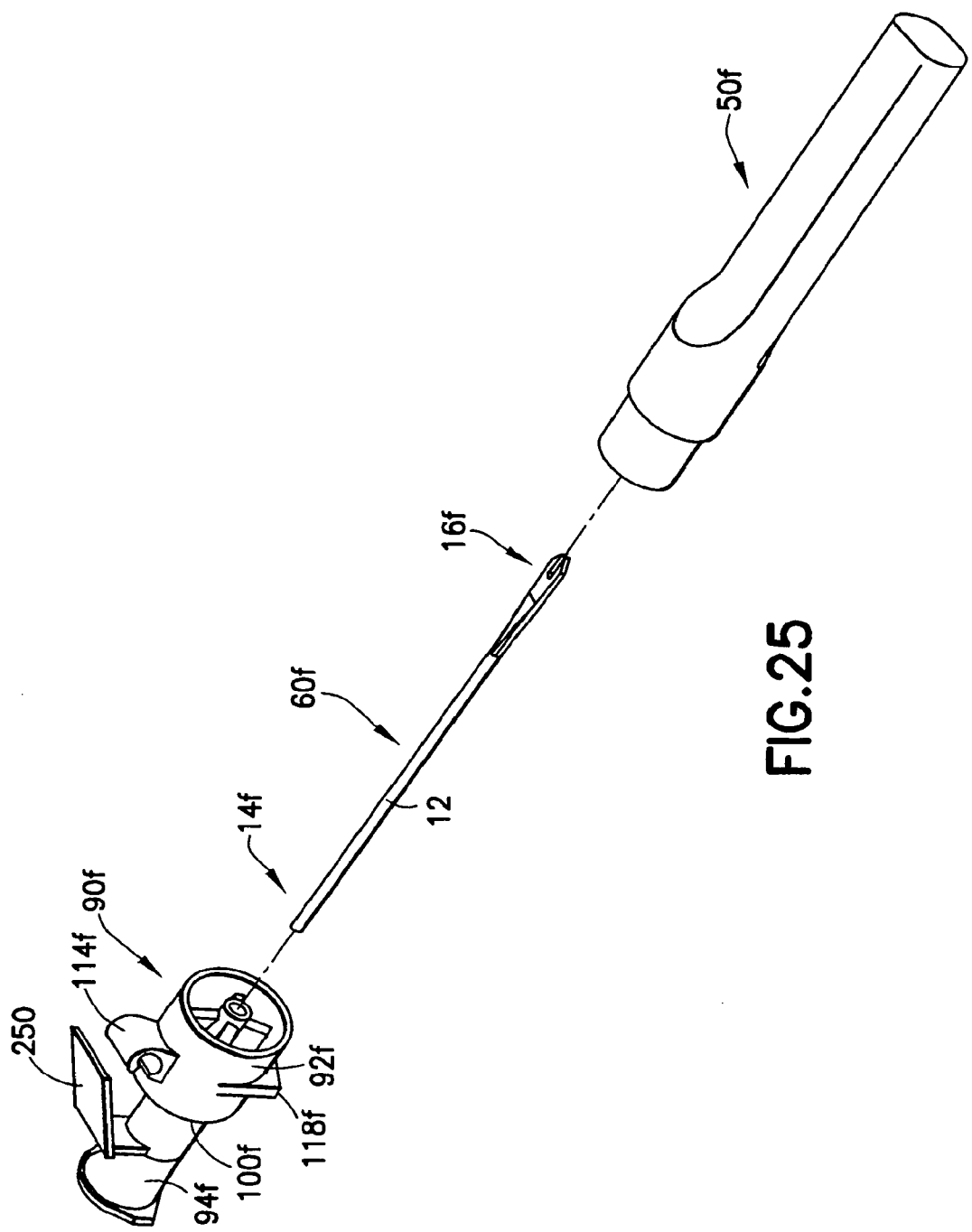
FIG. 25 is an exploded perspective view of the unit dose needle assembly as shown in FIG. 23.

The unit dose needle assembly 60f is preferably supported by the needle holding assembly 200 at the distal end 208 of needle holding member 202 via collar 90f. Collar 90f includes a forward annular skirt 92f at its distal end and a rearward annular skirt 94f at its proximal end. The forward annular skirt 92f may mate with a hub 22f. Preferably forward annular skirt 92f includes hub 22f integral within inner sidewall 96f as shown in FIG. 24. Thus, forward annular skirt 92f of collar 90f includes an internal bore 220 but having an internal diameter of approximately the same size as or a slightly larger size than the outer diameter of the proximal end 14f of the bifurcated needle 12f for accommodating the bifurcated needle 12f within internal bore 220.

Collar 90f including the unit dose needle assembly 90f within its forward annular skirt 92f, connects or joins needle holding assembly 200 through the rearward annular skirt 94f of the collar 90f. Rearward annular skirt 94f desirably includes an internal luer taper 222 which extends internally within a portion of rearward annular skirt 94f of collar 90f. Internal luer taper 222 is a female tapering surface which extends internally within at least a portion of rearward annular skirt 94f, for engagement with the male luer taper 214 of needle holding member 202. The rearward annular skirt 94f threadably engages with internal threads 218 defined in luer collar 216 at the distal end 208 of the needle holding member 202, with the female internal luer taper 222 frictionally engaging male external luer taper 214. In this manner, unit dose needle assembly 60f can be attached to needle holding assembly 200, which can provide shieldable needle assembly 60f with an appropriate handle portion for the assembly, thereby facilitating ease of use of the assembly.

Figure 26:
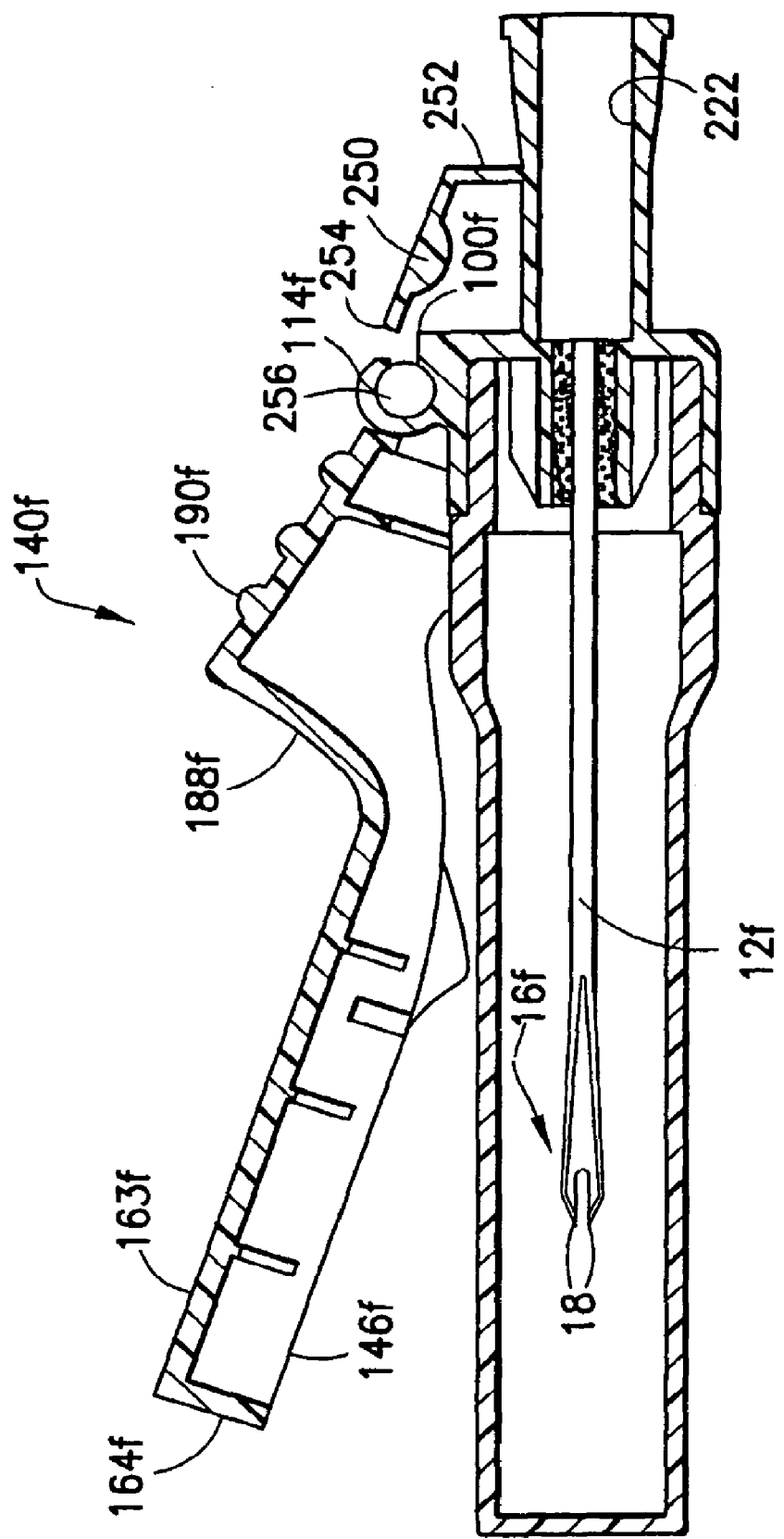
FIG. 26 is a side cross-sectional view of the shieldable needle assembly as shown in FIG. 25.
Figure 27:
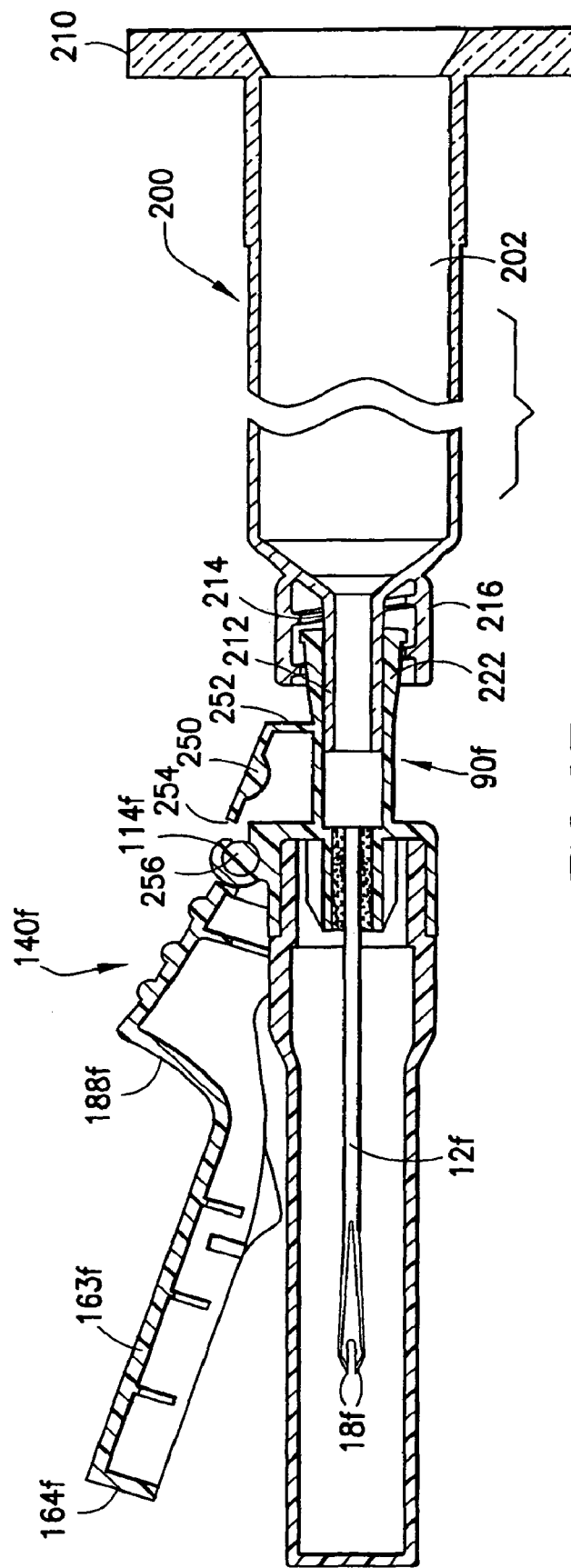
FIG. 27 is a side cross-sectional view of the shieldable needle assembly as shown in FIG. 23 including the needle holding assembly.
Figure 28:
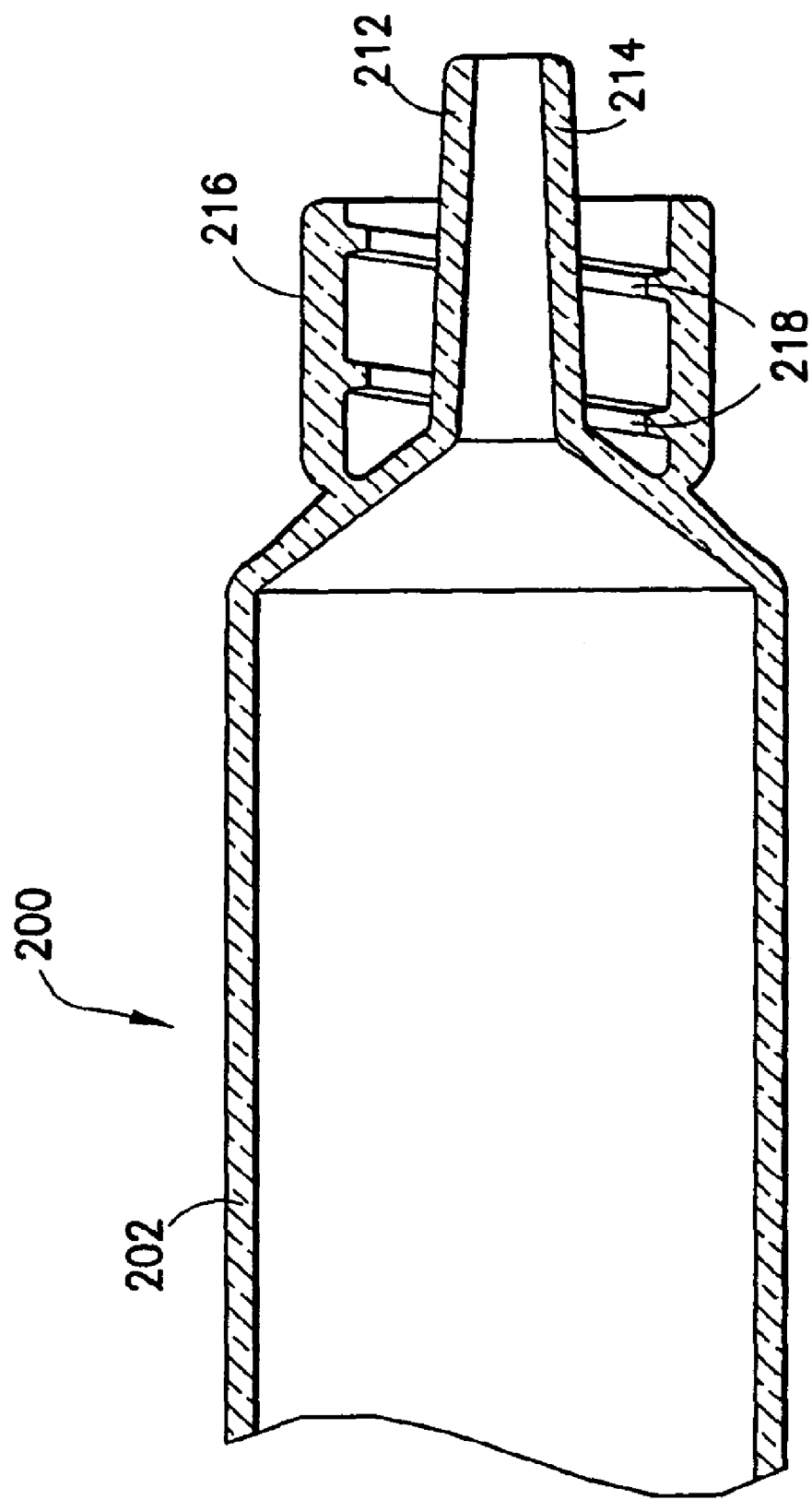
FIG. 28 is an enlarged cross-sectional view of a proximal end of the needle holding member in FIG. 23.

Collar 90f further includes a resilient projection 250. The projection 250 extends from collar 90f and comprises a hinged or cantilevered area represented by a hinge 252 that is integral with the collar 90f and a tab 254 that extends generally in the direction of the hook member 114f. Hinge 252 can be a living hinge or a portion configured to facilitate bending. The tab 254, in this embodiment is in opposing relation to the opening to a channel 256 when the projection 250 is unflexed, as shown in FIGS. 26-27. The projection 250 is configured such that the tab 254 preferably contacts the shoulder 100f of the collar 90f when projection 250 is urged towards the longitudinal axis of the collar 90f.

Figure 29:
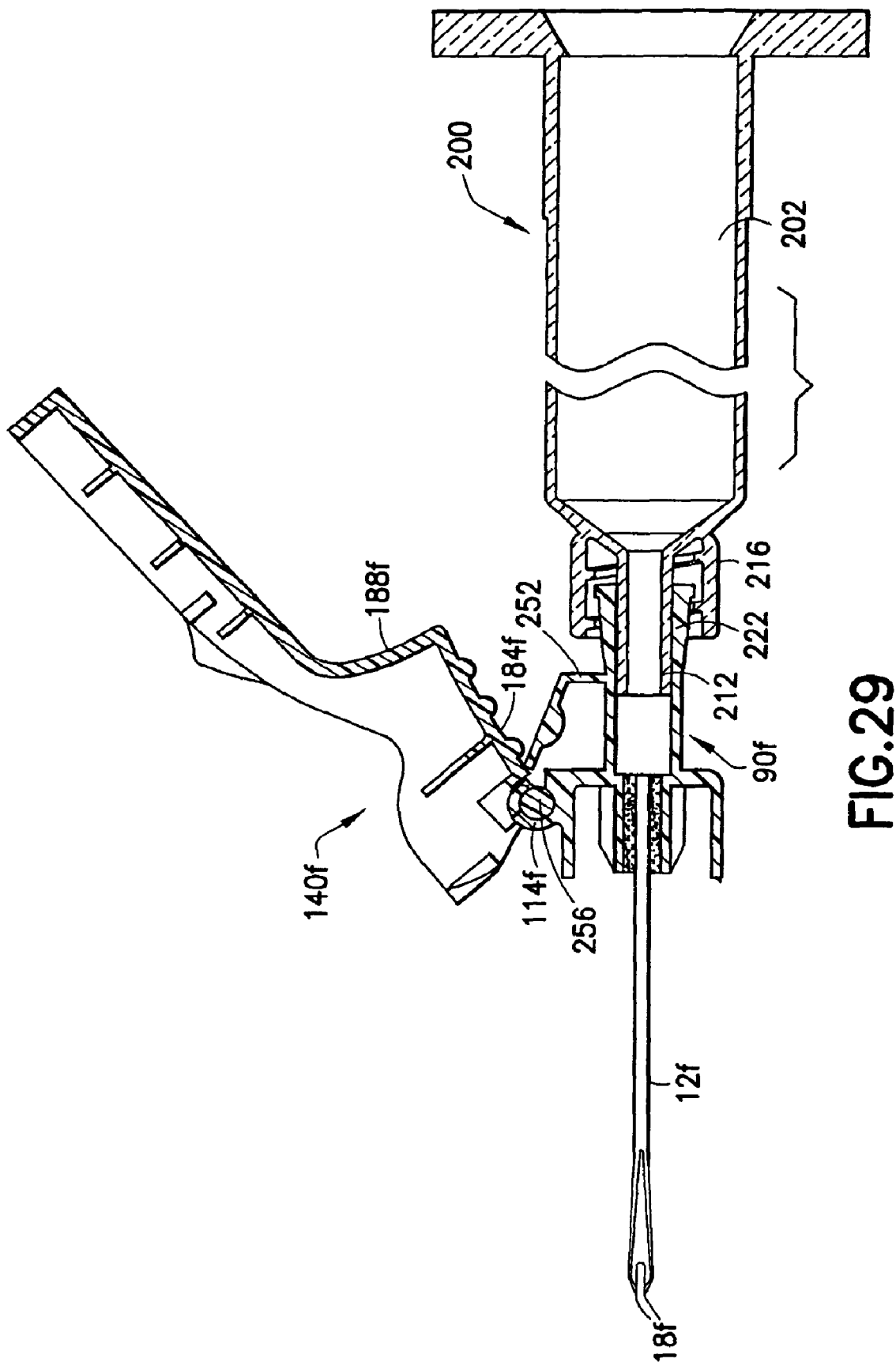
FIG. 29 is a side cross-sectional view of the shieldable needle assembly of FIG. 23 with the shield in a retracted position.
Figure 30:
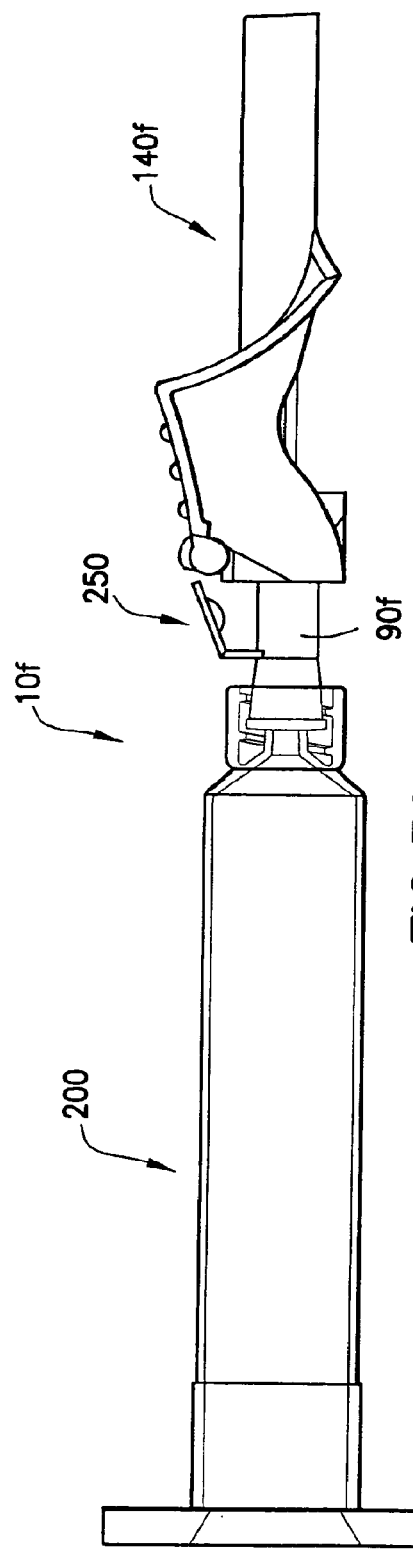
FIG. 30 is a side perspective view of the shieldable needle assembly of FIG. 23 with the needle packaging cover sleeve removed and the shield in a shielding position.
Figure 31:
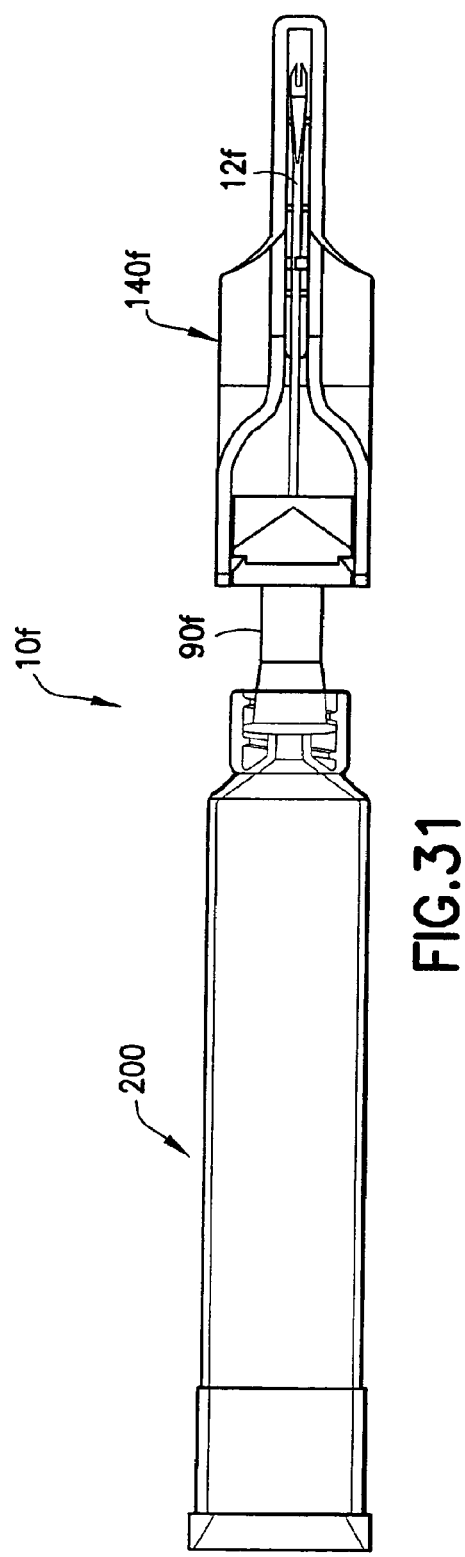
FIG. 31 is a bottom perspective view of the shieldable needle assembly of FIG. 23 shown with the needle packaging cover sleeve removed and the shield in a shielding position.

Referring to FIG. 29, a shield 140f as described above is pivotally attached to the collar 90f. The shield 140f is shown rotated back towards the needle holding assembly 200. The first ramp 84$f$ of the shield 140$f$ engages the tab 254 and displaces projection 250 since it is not a rigid structure. This flexibility is an important feature of the present embodiment since it reduces the possibility of dislodging the hanger bar 182$f$ pin from the channel 256 if the shield 140$f$ is urged against projection 250. A projection such as a ridge also helps prevent displacement or dislodging of the hinge pin from the channel during normal use. As the tab 250 tends to assume its resting position shown in FIG. 29 it will urge the shield 140$f$ about the hanger bar 182$f$ from the position shown in FIG. 29 to the preferred position, where projection 250 is unstressed, which is about a forty-five degree angle from the longitudinal axis of the bifurcated needle 12$f$ and needle holding assembly. While in this position the user is easily able to rotate the shield 140$f$ into the needle-protecting position while employing only one hand. There is sufficient space between the top finger guide area 172$f$ of the shield 140$f$ and the inclined surface of the tab 254 to allow the insertion of finger tip by most users, thereby initiating shield rotation. The shield 140$f$ is appropriately contoured elsewhere to protect the user while facilitating use of the shield 140$f$.

Resilient projection 250 further provides guidance to the user's finger to guide it radially distally outwardly into a smooth transition onto the shield 140$f$. Also, it is intended that that user should not apply excessive force to the shield 140$f$. Excessive and unnecessary force applied to the shield 140$f$ will force the shield 140$f$ against the projection 250 which, if not resilient, could act as a fulcrum to magnify forces on hanger bar 182$f$ which could easily break it or dislodge it from channel 256. However, because projection 250 is resilient, it pivots inwardly to reduce forces being applied to hanger bar 250. When the excessive and unnecessary force is discontinued, the resilient projection pivots outwardly moving the shield 140$f$ with it to the desired needle shield position for shielding the bifurcated needle 12$f$ after use.

In use, shieldable needle assembly 10 is provided as shown in FIG. 1 for use in administering a vaccine to a patient. Alternatively, unit dose needle assembly 60$a$, 60$b$, 60$c$, 60$d$, 60$e$, or 60$f$ may be provided for attachment to a shield assembly including collar 90$a$, 90$b$ 90$c$, 90$d$, 90$e$, or 90$f$ shield 140$a$, 140$b$, 140$c$, 140$d$, 140$e$ or 140$f$ and handle 70$a$, 70$b$, 70$c$, 70$d$, or 70$e$, or needle holding assembly 200 respectively, by threadably engaging the corresponding threaded surfaces of the respective hub and collar.

The user then grasps needle assembly 10 with handle 70 between finger and thumb at arcuate surfaces 72. In the embodiment of FIGS. 24-31, the user can grasp needing holding assembly 200 between finger and thumb or may grasp it with the entire palm, providing an effective grasping surface due to its size. Shield 140 is then rotated back by the user toward the handle 70 or needle holder 200. Then, as shown in FIG. 11, needle cover 50 is removed from the bifurcated needle 12. Needle assembly 10 can then be used for administration of a vaccine through the skin of a patient, using handle 70 as a handle for holding the assembly during use. For example, a unit dose of a vaccine contained within U-shaped channel 20 may be administered percutaneously to the patient by way of bifurcated needle 12. The unit dose of the vaccine may be contained within U-shaped channel 20 during packaging and prior to removal of needle cover 50, or the unit dose of the vaccine may be placed within U-shaped channel 20 after removal of needle cover 50 immediately prior to administration such as by accessing a vial containing multiple doses in liquid form where submersion of the U-shaped channel 20 into the vaccine retains the vaccine during removal of the bifurcated needle 12 from the vial. To administer the vaccine, the pointed prongs of bifurcated needle 12 penetrate the stratum corneum layer of the skin and deliver the vaccine contained within U-shaped channel 20 to the deep epidermis.

After administration of the vaccine is complete, the user easily pivotally rotates shield 140 from the open or retracted position toward bifurcated needle 12 to an intermediate position and then the user pushes on shield 140 at the top finger guide area 172 to move shield 140 into a final, non-retractable shielded position whereby needle 12 is trapped in longitudinal opening 160.

During pivotal rotation of shield 140 to the shielded position, barb dents 194 on inner surface 175 of parallel sidewalls 174 of shield 140 deflect over and are held by locking dents 118 of collar 90. The interengagement between barb dents 194 and locking dents 118 provide a locking structure for locking engagement between shield 140 and collar 90, thereby locking shield 140 in the shielded position and preventing pivotal rotation of shield 140 to the open or retracted position. Such locking further provides a tactile feel to the user that shield 140 has been rotated to the shielded position. Alternatively, it is contemplated that shield may include a latch or locking dent and the collar may include a detent or a barb dent for providing means for locking the shield in the shielded position.

Moreover, in embodiments including a needle locking mechanism such as a hook or arm 167, the needle snaps past arm 167 and is trapped when bifurcated needle 12 is contained within shield 140 as shield 140 is pivoted into the closed or shielded position. Alternatively, a gel material may be located in the shield near arm 167 so that when bifurcated needle 12 snaps past arm 167, it will come to rest within the gel material.

The means for locking, whether provided through the barb dent and latch protrusion of the shield and collar, through the needle locking mechanism of the hook attaching to the needle, or through both such features, is preferably irreversible, in that once the shield is pivoting to the shielding position and locked in place, it cannot be pivoted away to expose the needle without excessive force or displacement by the user.

The shieldable needle assembly of the present invention provides for a single use unit dose application of a vaccine. The needle assembly can be packaged as a sterile assembly for single use. The needle assembly can be packaged in an appropriate box and shelf carton as required for storage and shipment. Alternatively, the unit dose needle assembly and the shield assembly can be packaged separately in sterile packaging, and assembled just prior to use by the medical practitioner.

The shield, collar, handle and hub of the safety shield assembly of the present invention are comprised of moldable parts which can be mass produced from a variety of materials such as one or more moldable plastics including, for example, polyethylenes, polypropylenes, polyamides, polyesters, fluorinated polyethylenes, polyvinyl chloride, polystyrene, and the like. Materials will be selected which will provide the proper covering and support for the structure of the invention in its use, but which will also provide a degree of resiliency for the purpose of providing the cooperative movement relative to the shield and the collar of the assembly.

Desirably, the shield, collar, handle and hub are constructed of rigid polymeric materials, thereby providing a "hard pack" configuration to the needle assembly. This "hard-pack" configuration provides the benefits of a sterile barrier without requiring additional packaging. The inventive assembly also provides the benefit of an individual sterile package, which has in the past typically required paper packaging in a pouch or blister-type package. Further, bifurcated needles have traditionally been multiple use products which are re-sterilized in between uses. The hardpack configuration provides the benefit of a single use application and a sterile package in combination.

What is claimed is:

1. A shieldable unit dose needle assembly for administering a unit dose of a vaccine comprising:
    a needle holding member having a proximal end and a distal end, the distal end including a male tapering surface;
    a solid elongated unit dose needle having a proximal end and a prong end comprising at least two prongs configured to hold a unit dose of a vaccine;
    a shield in pivotal engagement with respect to said unit dose needle and pivotally movable between a retracted position pivotally spaced from said prong end of said unit dose needle and a shielded position encompassing said prong end of said unit dose needle; and
    a collar having a proximal end and a distal end including a needle end configured for holding the solid needle, said unit dose needle secured to and extending from said needle end of said collar, said collar surface including a proximal end having a female tapering surface in engagement with the male tapering surface at the distal end of said needle holding member, said collar providing for pivotal movement of said shield between said retracted position and said shielded position.

2. The needle assembly of claim 1, further comprising a projection member coupled to said collar and, a top surface including an outwardly and a distally extending tab.

3. The needle assembly of claim 2, wherein said shield includes a first ramp, said ramp of said shield being able to contact said projection member when said shield is rotated to said refracted position.

4. The needle assembly of claim 3, wherein said projection member is flexibly mounted to said collar.

5. The needle assembly of claim 1, wherein the unit dose needle comprises a bifurcated needle, wherein the prong end includes two pointed prongs which are capable of penetrating or abrading the skin of a patient, and wherein the prongs are separated by a U-shaped channel capable of holding the unit dose of a vaccine.

6. The needle assembly of claim 1, wherein the distal end of said needle holding member includes an annular collar having internal threads adjacent the male tapering surface, and wherein the proximal end of said collar includes structure for threaded engagement with the internal threads of the annular collar when the female tapering surface is in engagement with the male tapering surface.

7. The needle assembly of claim 1, further comprising means for preventing pivotal movement of said shield between the shielded position and the retracted position after the shield has been pivoted to the shielded position.

8. The needle assembly of claim 1, wherein the shield is pivotally connected to the collar through a hanger bar located on said shield and a hook arm located on said collar whereby said hanger bar engages with said hook arm so that said shield may be pivoted with respect to said collar between said refracted position and said shielded position.

9. The needle assembly of claim 1, wherein the needle holding member includes an annular flange extending about the proximal end thereof.

10. A shieldable unit dose assembly, comprising:
    a unit dose needle assembly comprising a collar having a female tapering surface at a proximal end thereof and a solid elongated unit dose needle secured to said collar and extending from a distal end thereof, the unit dose needle having a length capable of retrieving a unit dose of a vaccine from a separate container and having a patient end having a prong end comprising at least two prongs for containing and administering the unit dose of a vaccine; and
    a needle holding assembly having an elongated body with a proximal end and a distal end, the distal end including a male tapering surface in engagement with the female tapering surface of the collar of the unit dose needle assembly and an annular collar having internal threads in threaded engagement with corresponding structure on the proximal end of the collar, the needle holding assembly further including a shield in pivotal engagement with respect to said unit dose needle assembly and pivotally movable between a retracted position pivotally spaced from said patient end of said unit dose needle and a shielded position encompassing said patient end of said unit dose needle.

11. The needle assembly of claim 10, further comprising a projection member coupled to said collar and, a top surface including an outwardly and a distally extending tab.

12. The needle assembly of claim 11, wherein said shield includes a first ramp, said ramp of said shield being able to contact said projection member when said shield is rotated to said retracted position.

13. The needle assembly of claim 12, wherein said projection member is flexibly mounted to said collar.

14. The needle assembly of claim 10, wherein the needle holding assembly includes an annular flange extending about the proximal end thereof.

15. The needle assembly of claim 14, wherein the shield is pivotally connected to the collar through a hanger bar located on said shield and a hook arm located on said collar whereby said hanger bar engages with said hook arm so that said shield may be pivoted with respect to said collar between said retracted position and said shielded position.

16. The needle assembly of claim 10, wherein the unit dose needle comprises a bifurcated needle, wherein the prong end includes two pointed prongs which are capable of penetrating or abrading the skin of a patient, and wherein the prongs are separated by a U-shaped channel capable of holding the unit dose of a vaccine.

17. The needle assembly of claim 10, further comprising means for preventing pivotal movement of said shield between the shielded position and the retracted position after the shield has been pivoted to the shielded position.

* * * * *